(12) United States Patent
Mas et al.

(10) Patent No.: US 7,552,853 B2
(45) Date of Patent: Jun. 30, 2009

(54) LOW-PROFILE VASCULAR CLOSURE SYSTEMS AND METHODS OF USING SAME

(75) Inventors: Juan-Pablo Mas, Somerville, MA (US); Matthew F. Spurchise, Peabody, MA (US); Richard D. Lobello, Johnston, RI (US); Scott J. Epperly, East Bridgewater, MA (US); Kenneth A. Eliasen, Wrentham, MA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 394 days.

(21) Appl. No.: 11/626,633

(22) Filed: Jan. 24, 2007

(65) Prior Publication Data

US 2008/0173693 A1 Jul. 24, 2008

(51) Int. Cl.
*A61B 17/068* (2006.01)
(52) U.S. Cl. .................. 227/175.1; 227/19; 227/82; 606/142; 606/219
(58) Field of Classification Search .................. 227/19, 227/176.1, 175.1, 82, 83, 88; 606/139, 142, 606/143, 219
See application file for complete search history.

(56) References Cited

U.S. PATENT DOCUMENTS

| 5,392,978 | A | * | 2/1995 | Velez et al. .............. 227/177.1 |
| 5,413,584 | A | * | 5/1995 | Schulze ...................... 606/219 |
| 5,544,802 | A | * | 8/1996 | Crainich ................... 227/176.1 |
| 5,810,846 | A | * | 9/1998 | Virnich et al. .............. 606/142 |
| 5,941,890 | A | * | 8/1999 | Voegele et al. .............. 606/151 |
| 6,197,042 | B1 | * | 3/2001 | Ginn et al. .................. 606/213 |
| 6,391,048 | B1 | * | 5/2002 | Ginn et al. .................. 606/213 |
| 6,533,762 | B2 | * | 3/2003 | Kanner et al. ............... 604/175 |
| 6,767,356 | B2 | | 7/2004 | Kanner et al. |
| 6,926,731 | B2 | * | 8/2005 | Coleman et al. ............ 606/213 |
| 7,008,435 | B2 | * | 3/2006 | Cummins .................. 606/139 |
| 7,111,768 | B2 | * | 9/2006 | Cummins et al. ........ 227/175.1 |
| 7,115,138 | B2 | | 10/2006 | Renati et al. |
| 7,163,551 | B2 | * | 1/2007 | Anthony et al. ............. 606/219 |
| 2004/0093024 | A1 | | 5/2004 | Lousararian et al. |
| 2006/0217744 | A1 | | 9/2006 | Bender et al. |

FOREIGN PATENT DOCUMENTS

| WO | WO 02/19920 | 3/2002 |
| WO | WO03/013363 | 2/2003 |
| WO | WO2005/051171 | 6/2005 |
| WO | WO 2005/115251 | 12/2005 |

* cited by examiner

*Primary Examiner*—Scott A. Smith
(74) *Attorney, Agent, or Firm*—James F. Crittenden

(57) ABSTRACT

A closure device for an arteriotomy includes an elongate tube having a distal opening. The elongate tube has least two opposing longitudinal slots and a pair of opposing corners defined where each slot meets the distal opening. A staple is disposed within the tube, the staple having at least two opposing legs aligned with the at least two slots. Each slot is pinched together adjacent the distal opening such that the opposing corners of each slot converge to cover the tip of the respective staple leg to guard the staple tips against contact with the tissue track. The corners of each slot are separable to permit the respective staple leg to pass there between.

6 Claims, 19 Drawing Sheets

LOW-PROFILE VASCULAR CLOSURE SYSTEMS AND METHODS OF USING SAME

FIELD OF THE INVENTION

The present disclosure relates to system and method for closing an opening in a vessel wall after a medical procedure, and in particular, to a system and method for closing a puncture arteriotomy after an intra-luminal procedure such as catheterization.

BACKGROUND OF THE INVENTION

Catheters/catheterization procedures for diagnosis or treatment of cardiovascular and/or peripheral vascular diseases are well known, and typically involve the Seldinger technique to make insertions through layers of tissue and through a wall of the femoral artery. After a diagnostic or interventional catheterization, the arteriotomy puncture formed by the catheter or introducer sheath must be closed. The puncture opening in the artery typically ranges from 5 French (0.0655 inch, 1.67 mm) such as for a diagnostic angiography procedure to as large as 30 French (0.393 inch, 10.00 mm) for an interventional procedure such as implanting an inferior vena cava (IVC) filter. Traditionally, intense pressure has been applied to the puncture site for at least 30-45 minutes after removal of the catheter. Patients who have had a femoral artery puncture are then required to remain at bed rest, essentially motionless and often with a heavy sandbag placed on their upper legs, for several hours to ensure that the bleeding has stopped. Other approaches include the use of a thrombotic or collagen plug or slurry, and/or other suturing methodologies for sealing the puncture. Also known are systems and methods for blind delivery, viz., without direct visualization, of a staple or clip to gather and hold together sides of the arteriotomy. However, these closure systems typically deliver, or perform the closure modality via a sheath, which holds the tissue track open. Therefore, there is a need for a low-profile closure system.

BRIEF SUMMARY OF THE INVENTION

A method for closing an arteriotomy in a wall of a vessel of a body after an intra-luminal procedure is disclosed. The terms "distal" and "proximal" are used in the specification with respect to a position or direction relative to the treating clinician. "Distal" or "distally" are a position distant from or in a direction away from the clinician. "Proximal" and "proximally" are a position near or in a direction toward the clinician. The method may be practiced without a sheath in place in the tissue track. A guidewire from the intra-luminal procedure remains in the vessel or is replaced with another guidewire. A procedural sheath, if used, is removed from the patient. A dilator and a guiding system are advanced together along the guidewire into the body tissue, through the arteriotomy and are into the vessel lumen. The guiding system includes at least two stabilization wire guides, each stabilization wire guide having a deployable retention foot disposed at a distal portion thereof. The guiding system is deployed within the vessel lumen such that the retention feet can be pulled back against an inner surface of the vessel wall. The guidewire and dilator are withdrawn from the lumen and the body tissue, leaving only the guiding system in place. A closure system is advanced along the guiding system to a position proximal to the arteriotomy. The closure system includes a center tube housing a stapler, the center tube having at least two side tubes for riding along the stabilization wire guides. The stapler is then activated to close the arteriotomy and the guiding system and closure system are withdrawn from the lumen and the body.

An embodiment of the stapler includes an elongate hollow shaft having at its distal end a pair of opposing actuation tips that define a staple chamber there between. An anvil extends into the staple chamber from one of the actuation lips to retain and deform a staple. An elongate driver is slidably disposed in the hollow shaft. A staple includes a pair of opposing legs proximally coupled by a bend and having an expansion ramp extending from each leg toward the other leg. The staple may be opened and/or closed by plastic or elastic deformation. When the closure system is disposed adjacent to the arteriotomy, an operator mechanism moves the driver longitudinally relative to stapler shaft such that the driver advances the staple between the actuation tips. The staple expansion ramps ride and spread apart along the anvil, thereby opening the staple. As the operator continues to push the driver longitudinally, the staple expansion ramps clear the anvil, permitting the staple to close. In an embodiment of the stapler, the driver closes the staple by deforming the staple bend against the anvil. In another embodiment, of the stapler, the staple is elastically self-closing. A staple release mechanism is actuated to spread the actuation tips apart, creating a gap through which the staple is released from the anvil.

In an embodiment of the closure system, a distal portion of the center tube is pinched such that it separates the staple tips from the tissue track during delivery to the arteriotomy site. When the staple is deployed, the staple spreads the pinched portion apart.

In another embodiment of the closure system, a frangible cap is disposed over the distal opening of the center tube. The frangible cap separates the staple tips from the tissue track during delivery to the arteriotomy site. When the staple is deployed, the staple perforates or fractures the frangible cap. Optionally, a portion of the frangible cap tears away from the center tube to form a pledget that is retained against the arteriotomy by the staple.

BRIEF DESCRIPTION OF DRAWINGS

The foregoing and other features and advantages of the present disclosure will be apparent from the following description of the disclosure as illustrated in the accompanying drawings. The accompanying drawings, which are incorporated herein and form a part of the specification, further serve to explain the principles of the disclosure and to enable a person skilled in the pertinent art to make and use the disclosure. The drawings are not to scale.

DETAILED DESCRIPTION OF THE INVENTION

Low Profile Guiding System

Figure 1:
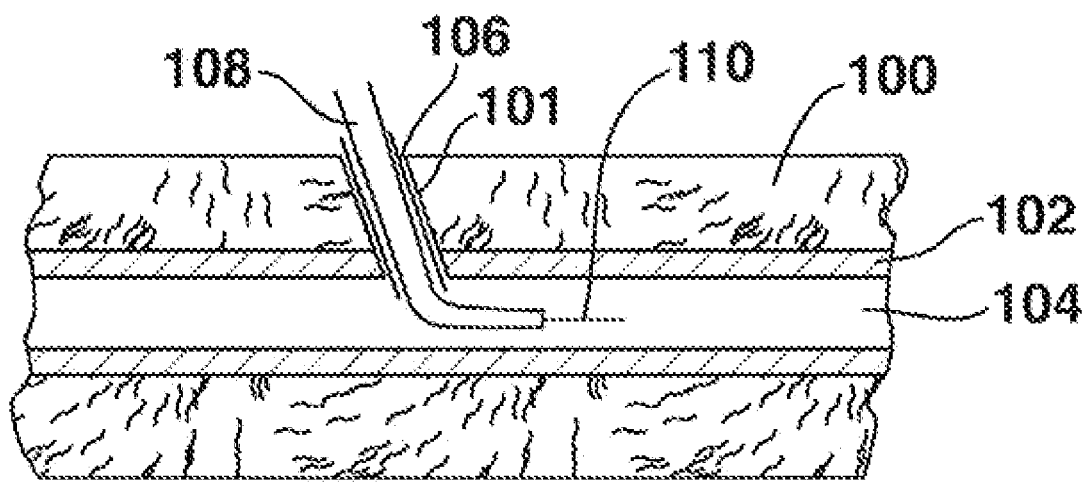
FIG. 1 is a cross-sectional view of body tissue including a vessel with a procedural device inserted in the vessel.

Specific embodiments of the present disclosure are now described with reference to the figures, where like reference numbers indicate identical or functionally similar elements. The present disclosure is directed to a device and method for closing an arteriotomy after a procedure in which a vessel was punctured to gain access to the vessel lumen. FIGS. 1-10 show cross-sectional views of body tissue 100 with a vessel 102 disposed therein. FIG. 1 shows a procedural device 108, such as a balloon catheter, disposed partially within a lumen 104 of vessel 102. The distal end of procedural device 108 is shown riding along a guidewire 110. Procedural device 108 passes through a procedural sheath 106, which maintains access to lumen 104 through a tissue track 101 in tissue 100 and arteriotomy 132 in the wall of vessel 102.

Figure 2:
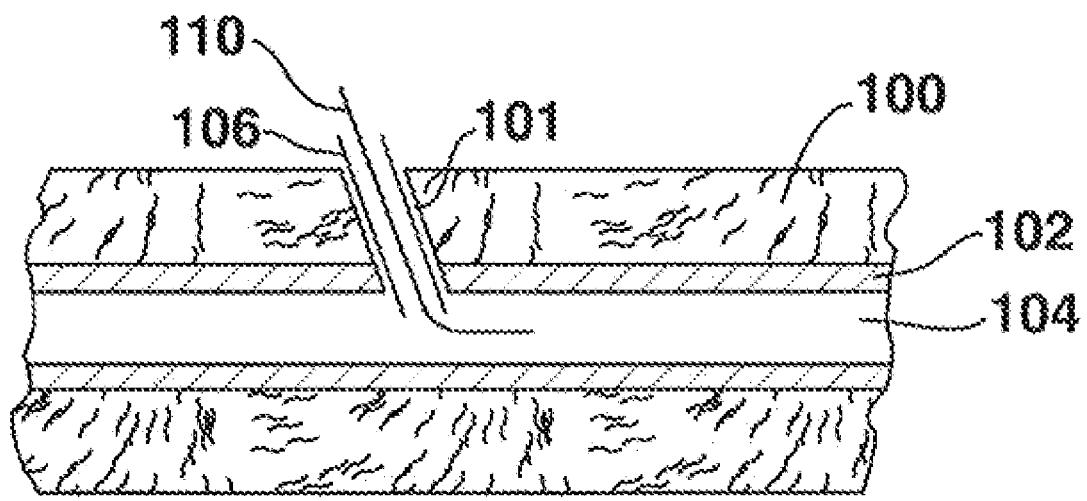
FIG. 2 is cross-sectional view of body tissue including a vessel with a guidewire inserted in the vessel.
Figure 3:
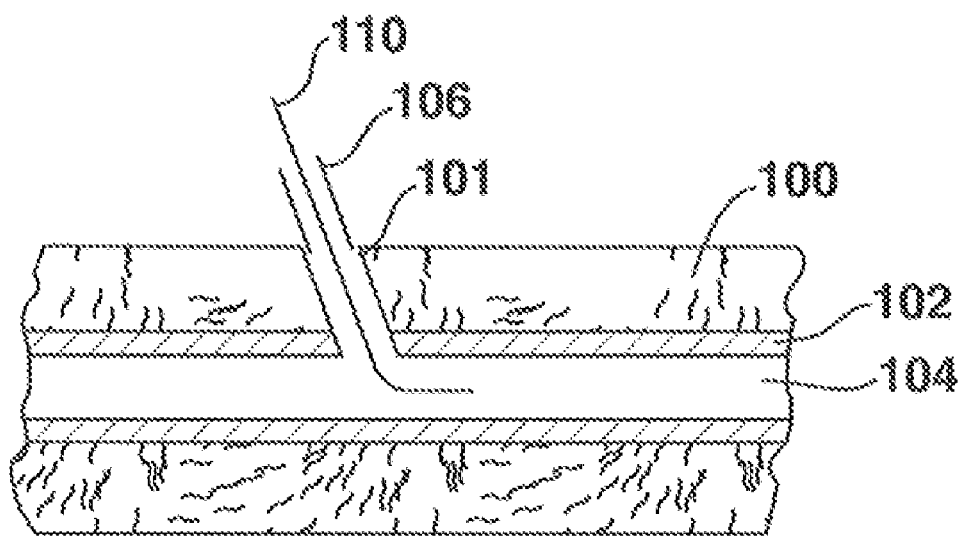
FIG. 3 is cross-sectional view of body tissue including a vessel with a procedural sheath being removed from the tissue.

As the intra-luminal procedure, such as balloon angioplasty, is completed, procedural device 108 is removed from vessel 102 and tissue track 101 via procedural sheath 106, as shown in FIG. 2. Guidewire 110 remains in place partially disposed within lumen 104 of vessel 102. As shown in FIG. 3, procedural sheath 106 is removed from lumen 104, arteriotomy 132, and tissue track 101, leaving guidewire 110 in place. Although tissue track 101 and arteriotomy 132 are shown in FIG. 3 as being maintained in an open state, in practice, tissue track 101 and arteriotomy 132 will tend to at least partially close around guidewire 110 when procedural sheath 106 is removed.

Figure 4:
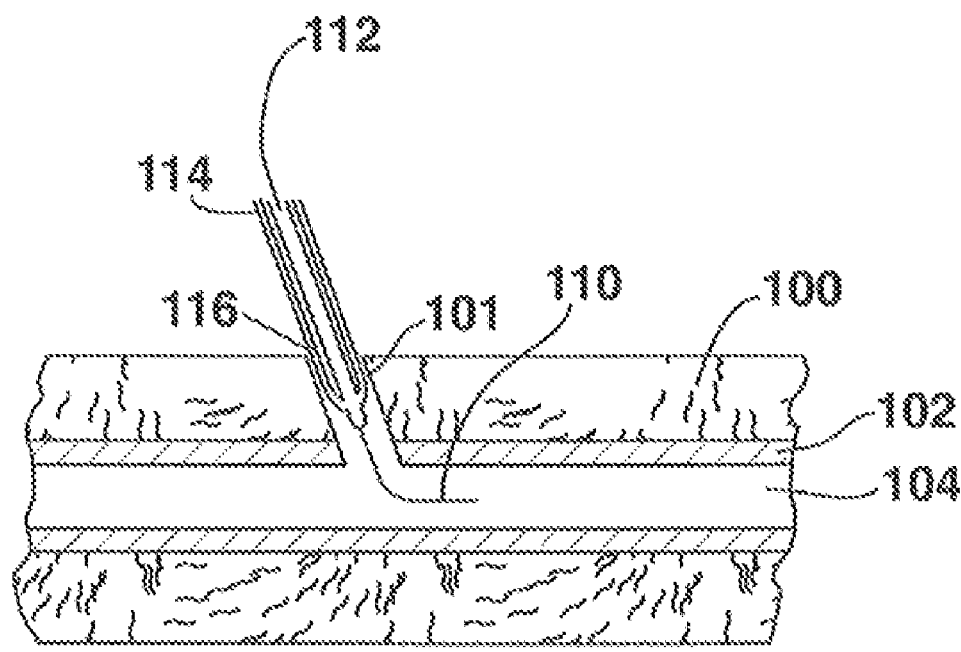
FIG. 4 is a cross-sectional view of an embodiment of a dilator and retention system being inserted into body tissue.
Figure 5:
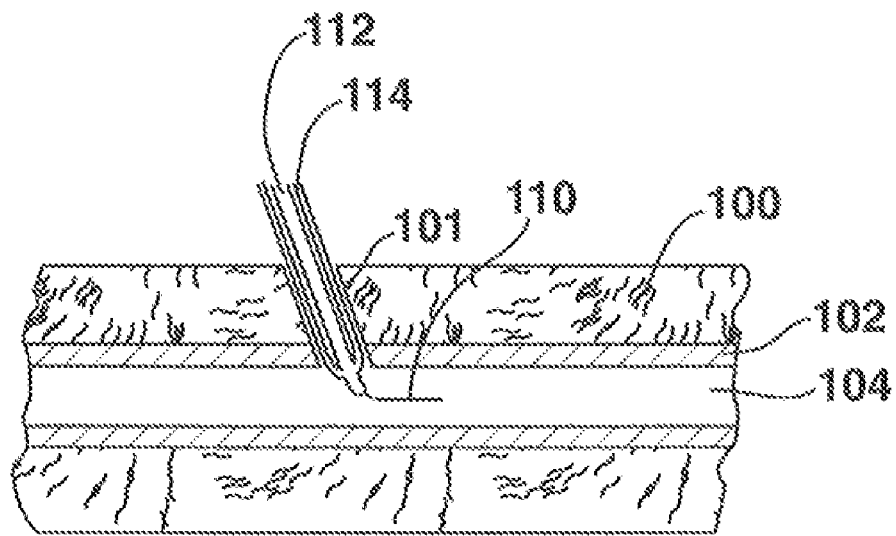
FIG. 5 is a cross-sectional view of the dilator and retention system of FIG. 4 being inserted into a vessel through an arteriotomy.

A vascular closure system of the disclosure is used to close arteriotomy 132, as follows. As shown in FIG. 4, a dilator 112 is guided along guide wire 110 into tissue track 101. Provided with dilator 112 is a pair of stabilization wire guides 114. Stabilization wire guides 114 ride along an outside surface of dilator 112. Distal portions of stabilization wire guides 114 are inserted into respective openings 116 in dilator 112 so that stabilization wire guides 114 advance with dilator 112 into tissue track 101. As shown in FIG. 5, dilator 112 and stabilisation wire guides 114 are advanced farther along guidewire 110 into lumen 154. As dilator 112 is advanced into tissue track 101 and arteriotomy 132, dilator 112 opens tissue track 101 and arteriotomy 132.

Figure 6:
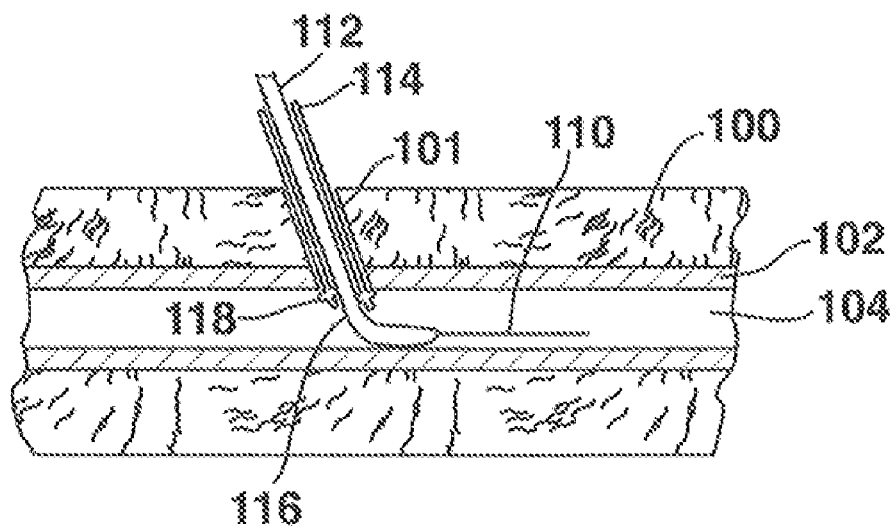
FIG. 6 is a cross-sectional view of the dilator and retention system of FIG. 4 with stabilization wire guides released from the dilator.

As shown in FIG. 6, dilator 112 and stabilization wire guides 114 are advanced far enough into lumen 104 of vessel 102 to ensure that retention feet 118 are intraluminal prior to their deployment. Numerous methods are known to those of skill in the art to measure or accurately indicate the intraluminal position of portions of a vascular closure device. In one known device, intraluminal position of the device may be indicated by blood entering the device through an inlet port positioned within the vessel lumen, the blood flowing through a passageway in the device, and the blood finally emitting from the device as a visible "flashback" out of art exit port external to the patient. In an alternative known type of position indicator, the device may have an enlarged physical stop for abutting against the external wall of the blood vessel to provide a tactile indication of the position of the device with respect to the vessel wall.

Dilator 112 is advanced farther into lumen 104 of vessel 102 while stabilization wire guides 114 are restricted from movement. This relative movement between dilator 112 and stabilization wire guides 114 causes the distal portions of stabilization wire guides 114 to be exposed or released from openings 116 in dilator 112. Stabilization wire guides 114 are manipulated or deployed to form retention feet 115 in the distal portions thereof. Retention feet 118 may be formed in various ways as would be known to those of ordinary skill in the art, for example, the ways described in FIGS. 49-57 of U.S. Pat. No. 6,767,356 to Kanner et al., the entire disclosure of which is incorporated herein by reference. Retention feet 118 are pulled back against an inner wall 120 of vessel 102, thus providing temporary anchoring for stabilization wire guides 114, and also providing an indication of the location, or depth of inner wail 120 relative to other components of the vascular closure system. For convenience of illustration, FIGS. 5-10 show a pair of stabilization wire guides 114 aligned along the axis of vessel 102. In actual use however, such a pair of stabilization wire guides 114 will typically be aligned transverse to the axis of vessel 102 and positioned at the ends of the slit that naturally forms generally perpendicular to the length of the vessel when arteriotomy 132 is formed in the wall of vessel 102, as described in the above-mentioned Kanner '356 patent. Such transverse alignment of stabilization wire guides 114 within arteriotomy 132 is especially typical when stabilization wire guides 114 are spread apart by closure system 122 as described below.

Figure 7:
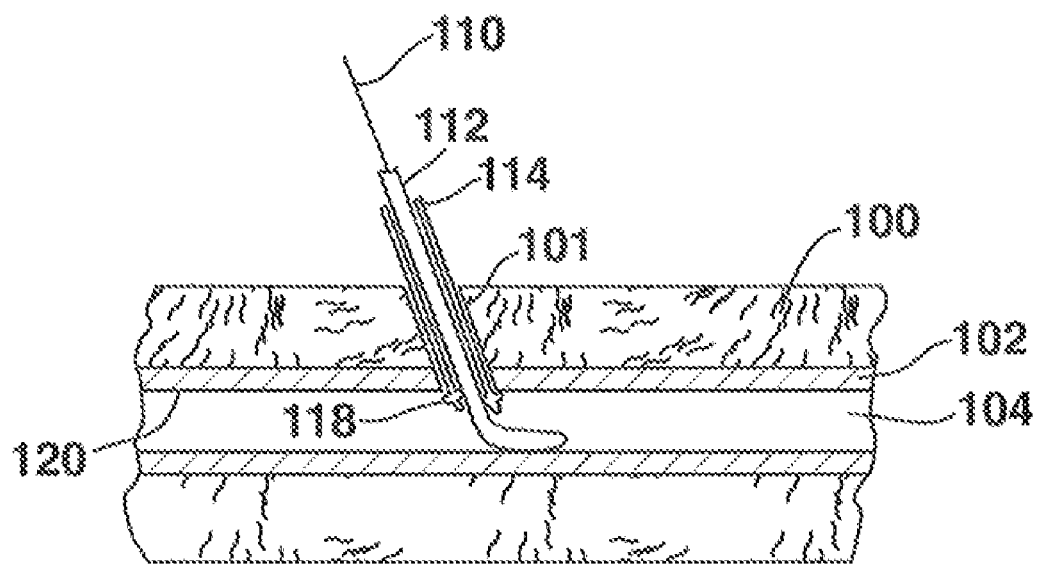
FIG. 7 is a cross-sectional view of retention feet of the stabilization wire guides of FIG. 6 deployed within a vessel and the guidewire being removed from the vessel and body tissue.
Figure 8:
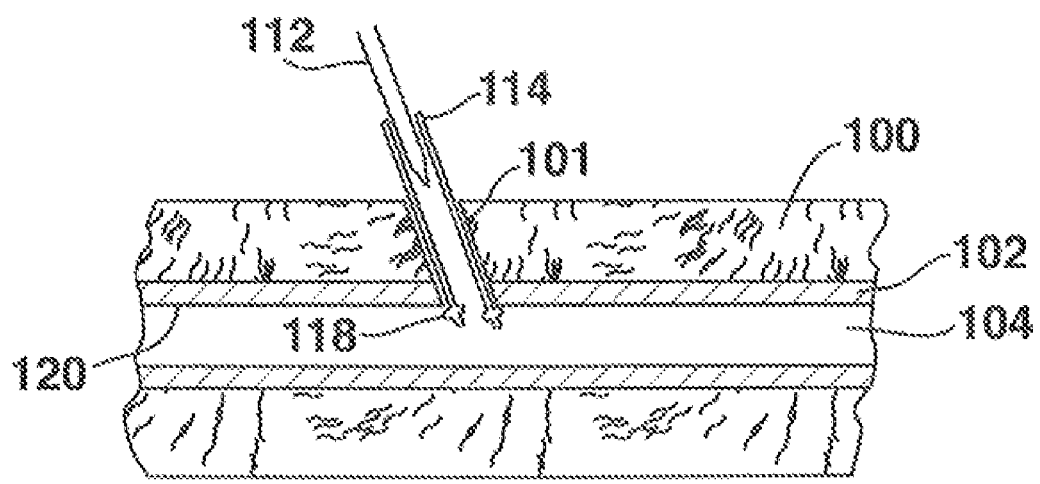
FIG. 8 is a cross-sectional view of the retention feet of FIG. 7 deployed and the dilator being removed from the vessel and body tissue.
Figure 9:
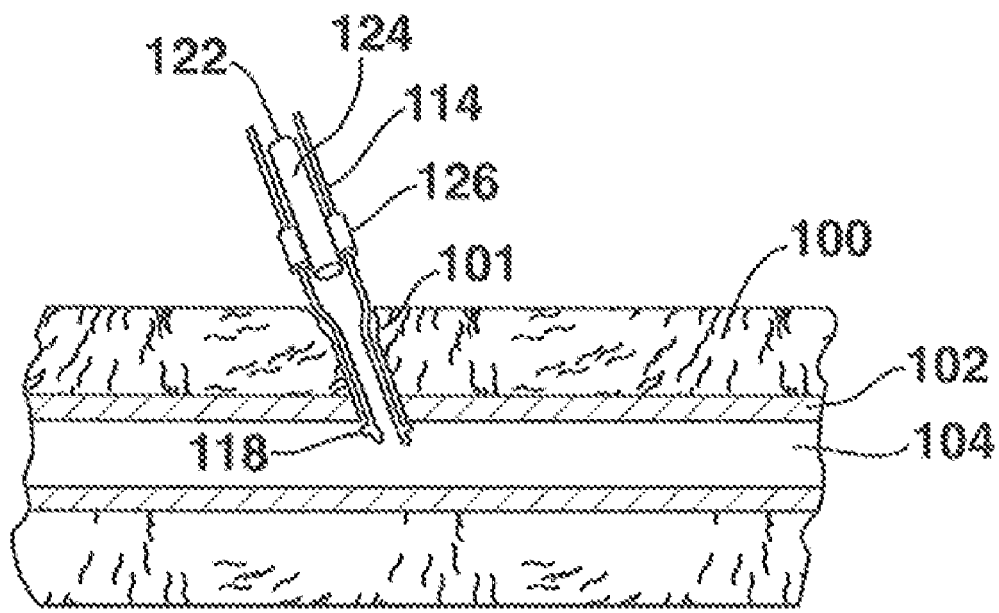
FIG. 9 is a cross-sectional view of an embodiment of a closure system as it enters the body tissue.
Figure 10:
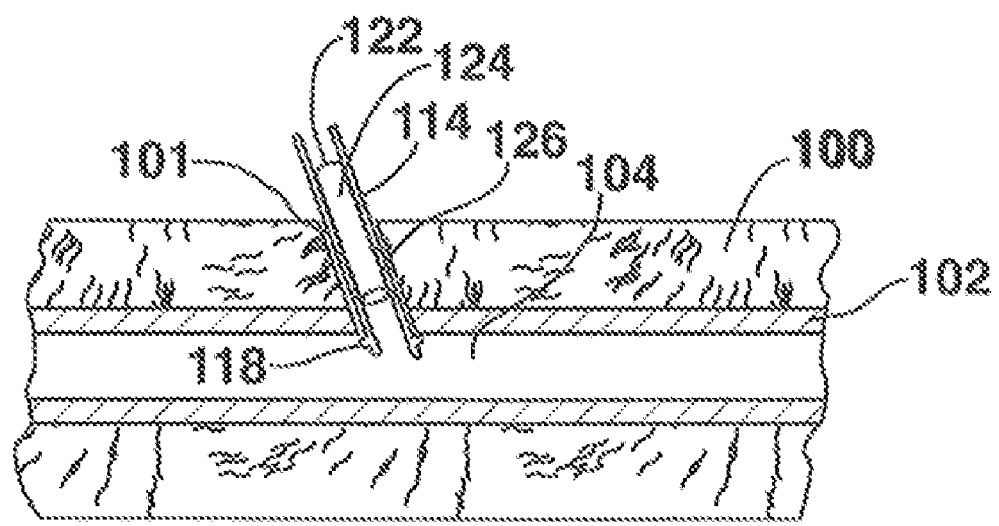
FIG. 10 is a cross-sectional view of the closure system of FIG. 9 as it reaches a location just outside of the vessel, adjacent the arteriotomy.

Referring to FIGS. 7 and 8, guidewire 110 and dilator 112 are removed from lumen 104, arteriotomy 132 and tissue track 101, leaving only stabilization wire guides 114 extending through tissue track 101 and arteriotomy 132 into lumen 104. Stabilization wire guides 114 provide guidance for insertion of a closure system. Referring to FIGS. 9 and 10, a closure system 122 is slidably mounted onto stabilization wire guides 114 so that a distal portion of closure system 122 can ride along stabilization wire guides 114 to a location within tissue track 101 spaced proximally from vessel 102. Closure system 122 includes an elongate stapler 128 carried slidably within a center tube 124. Two or more relatively short side tubes 126 are coupled parallel to the distal portion of center tube 124 on opposing sides thereof. In an embodiment, center tube 124 may be 30 cm long and side tubes may be 2 cm long. Center tube 124 and side tubes 126 will separate stabilization wire guides 114 when closure system 122 is advanced there along. Separating stabilization wire guides 114 applies tension along the long axis of slit-shaped arteriotomy 132 such that tissue along both sides of arteriotomy 132 tends to come together for engagement by a closure system, as described in the above-mentioned Kanner '356 patent.

Figure 11:
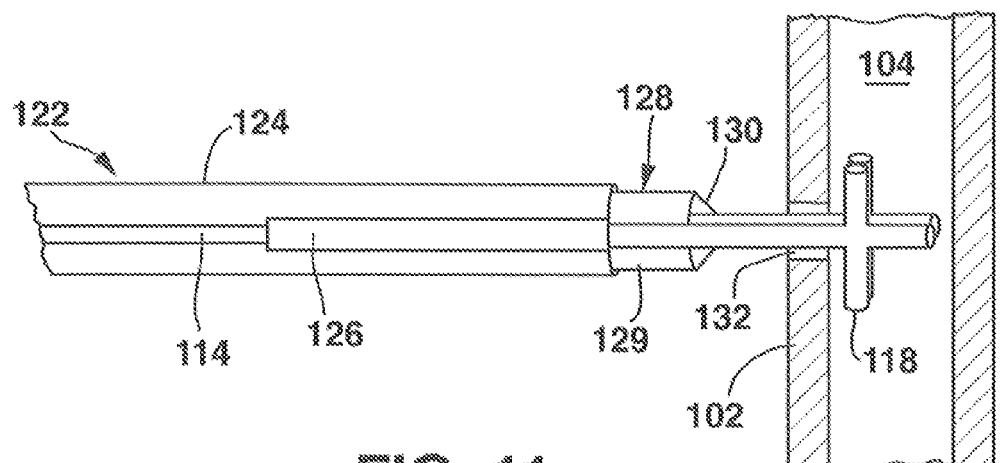
FIG. 11 is a perspective view of the closure system of FIG. 9 with expansion tips extended beyond a distal opening of a center tube.

FIG. 11 shows a side view of an embodiment of the present disclosure. Vessel 102 is shown in longitudinal cross-section and tissue 100 has been excluded for convenience of illustration. With retention feet 118 deployed within lumen 104 of vessel 102, closure system 122 is advanced toward arteriotomy 132 until the distal end of closure system 122 is stopped extraluminally at a preset distance from retention feet 118. The distance between the distal end of closure system 122 and retention feet 118 may be preset in a mechanism (not shown) coupled to the proximal ends of stabilization wire guides 114 and center tube 124. After confirming the apposition of retention feet 118 against inner wall 120 of vessel 102, as shown in FIG. 11, stapler 128 may be advanced distally within center tube 124 to expose a pair of actuation tips 129 and a staple 130 held there between.

Figure 12:
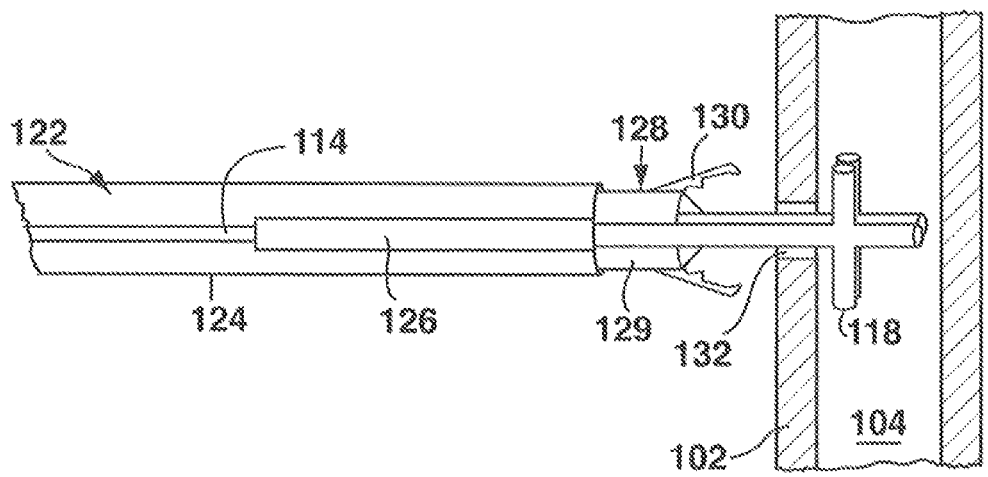
FIG. 12 is a perspective view of the closure system of FIG. 9 as a staple is being deployed.
Figure 14:
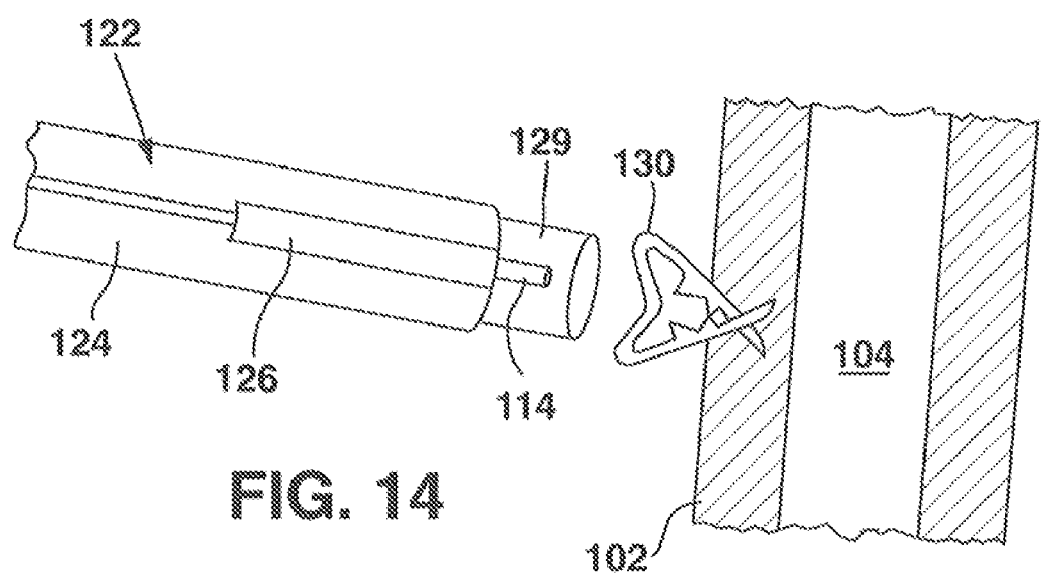
FIG. 14 is a perspective view of the closure system of FIG. 9 with the staple deployed and the center tube and stabilization wire guides being removed from the body tissue.

As shown in FIG. 12, two staple tips 139 of staple 130 are expanded laterally and are extended distally from between actuation tips 129 to pierce vessel tissue on either side of arteriotomy 132. Note that, whereas side tubes 126 and stabilization wire guides 114 are described as being disposed on "sides" of stapler 128, then "lateral" expansion of staple tips 139 means the tips expand toward the top and bottom of stapler 128. It will be understood by one of skill in the art that top, bottom and side are terms used only to assist the reader in understanding the relative positions of the components of the disclosure. Staple tips 139 are then closed to gather or pucker the engaged tissue, thus closing arteriotomy 132. Staple 130 is released from stapler 128 to remain embedded in vessel 102. Described further below are several embodiments of the disclosure that are suitable for releasing a staple from a stapler. Stabilization wire guides 114 and closure system 122, except for staple 130, are then removed from the body, as shown in FIG. 14. Actuation tips 129 and staple 130 may be conventional as would be known to one of ordinary skill in the art, such as the actuating tip portion of a stapler and the staple shown in FIGS. 67-71 of the above-mentioned Kanner '356 patent.

First Stapler Embodiment

Figure 15:
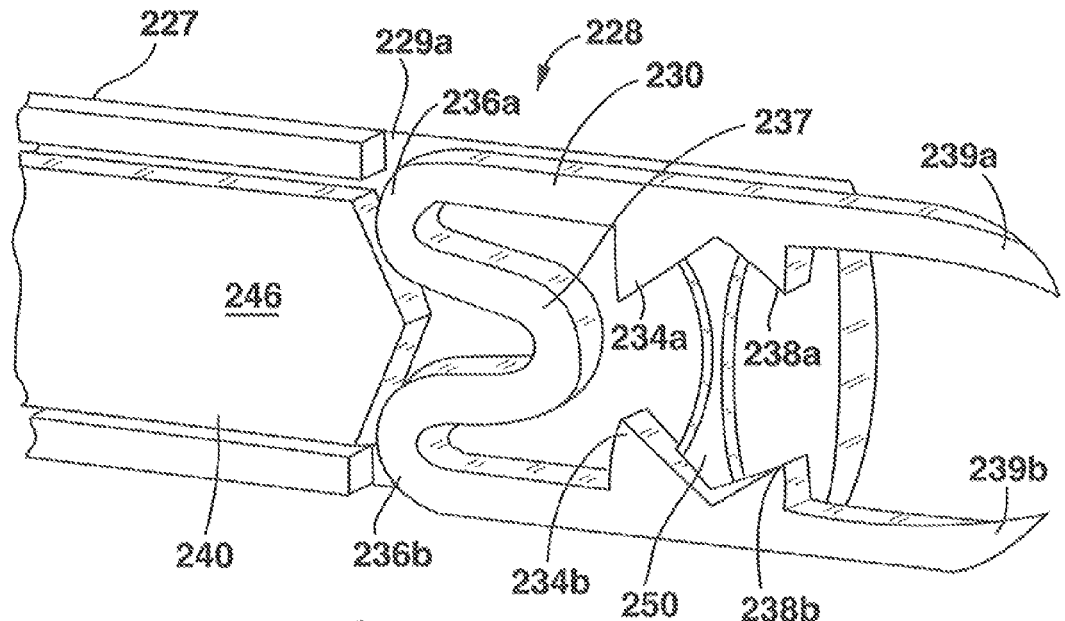
FIG. 15 is a perspective cut-away view of an embodiment of a stapler of the present disclosure.
Figure 16:
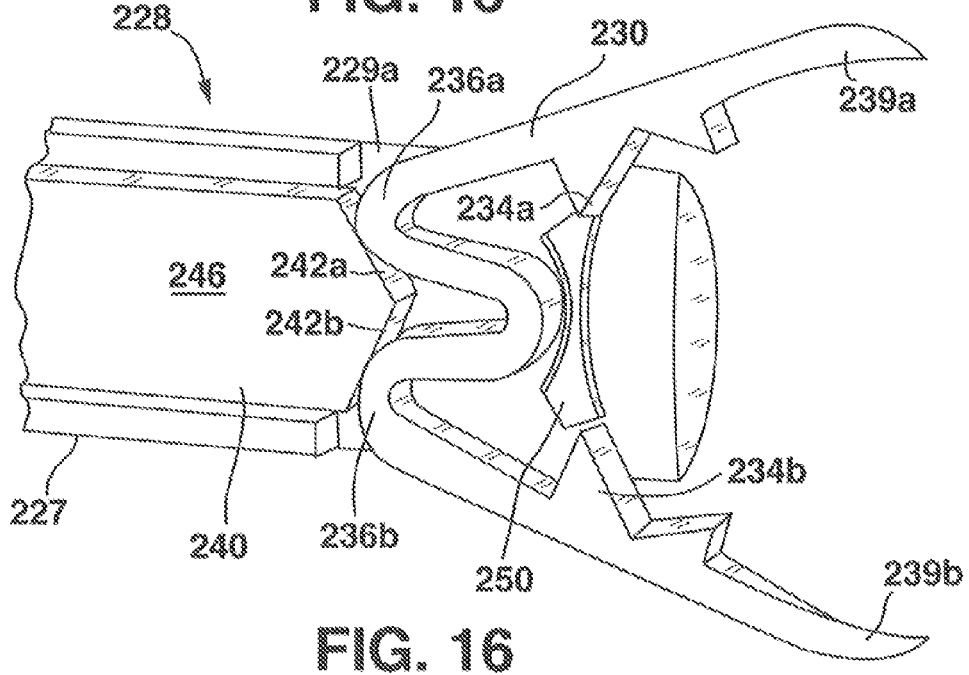
FIG. 16 is a perspective cut-away view of the stapler of FIG. 15 with the staple being deployed.
Figure 17:
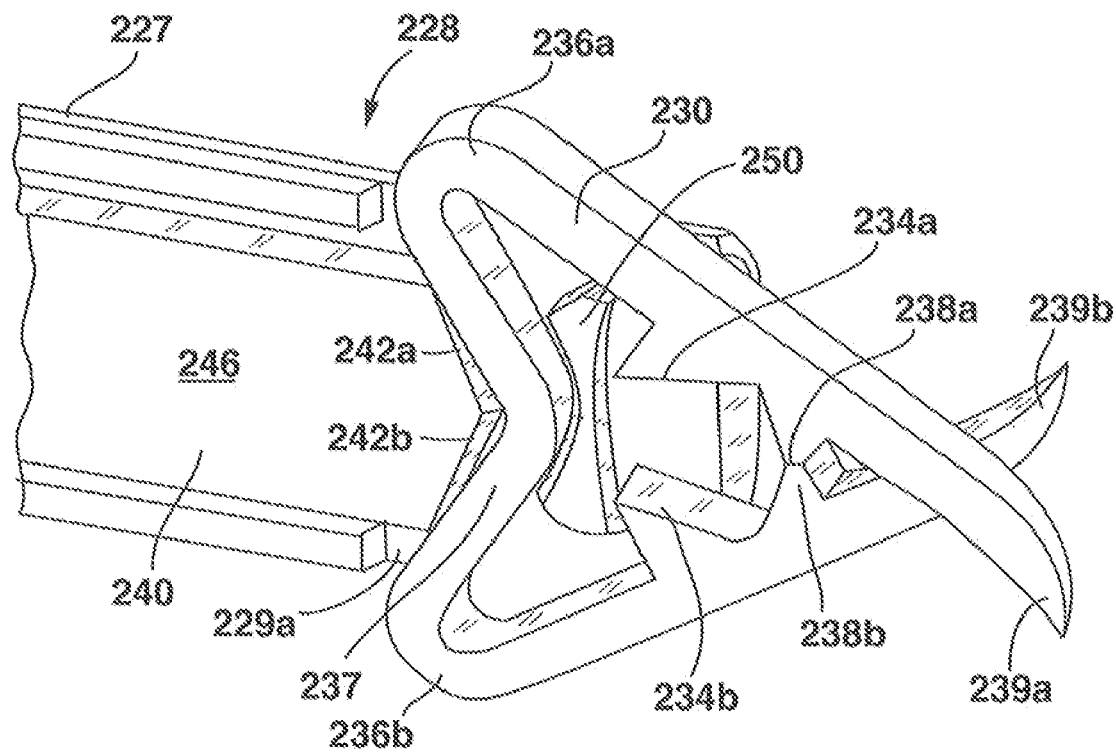
FIG. 17 is a perspective cut-away view of the stapler of FIG. 15 with the staple closed after deployment.
Figures 18, 19:
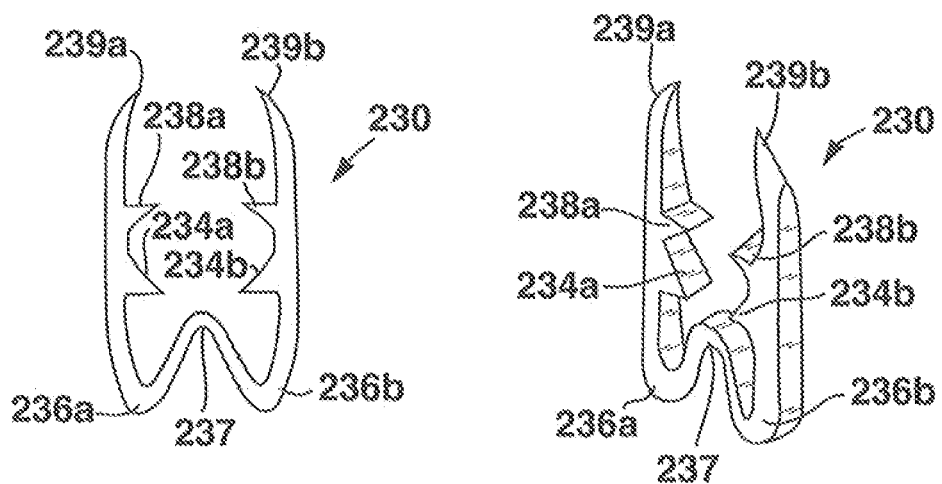
FIG. 18 is a plan view of an embodiment of a staple of the present disclosure.
FIG. 19 is a perspective view of the staple of FIG. 18.
Figure 46:
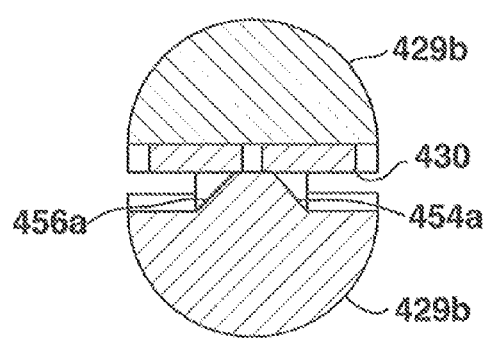
FIG. 46 is an alternative embodiment of the stapler of FIGS. 42-44, shown in a transverse cross-section view along line 46-46 of FIG. 44 with the actuation tip that was cut away from FIGS. 42 and 44.
Figure 47:
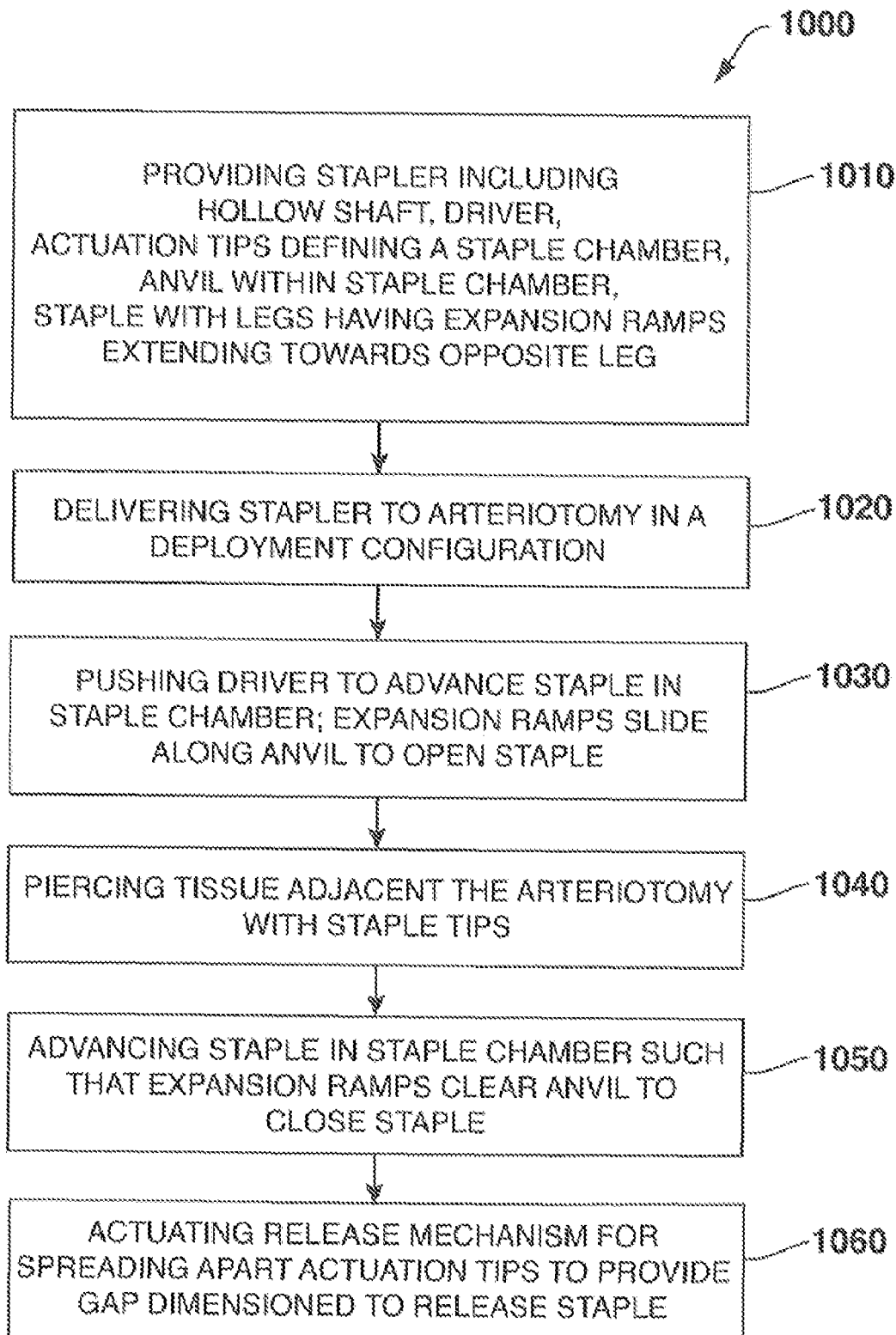
FIG. 47 is an outline of a method of using a vascular closure system in accordance with the disclosure.

FIGS. 15-19 show an embodiment of a stapler 228 of the present disclosure. In particular, FIG. 15 is a cut-away perspective view of stapler 228. FIG. 47 outlines a method 1000 of using staplers in accordance with the disclosure, including stapler 228. Stapler 228 includes an elongate hollow shaft 227. At the distal end of hollow shaft 227 is a pair of flat-sided, opposing actuation tips 229 (only one tip 229a is shown in FIGS. 15-17). The flat sides of actuation tips 229 face each other and are spaced apart to provide a passageway for slidably receiving a flat distal portion of an elongate driver 240, and to provide an open-sided staple chamber for holding at least a proximal portion of a staple 230. The open sides of the staple chamber are oriented toward the top and bottom of stapler 228. For example, see staple chamber 345 in FIG. 24. The distal end of driver 240 has a pair of tip edges 242 arranged to form an axially symmetrical pointed tip for abutment against a proximal end of staple 230. An anvil 250 for deforming or deflecting staple 230 is fixed within the staple chamber. Single anvil 250 may be dimensioned to substantially span the staple chamber, as illustrated in FIG. 46, and may be integrally formed with or attached to actuation tip 229a, without being affixed to opposite actuation tip 229b. Alternatively, anvil 250 may be formed by two mating anvil halves, each anvil half being integral with or attached to actuation tip 229a or 229b, respectively. Driver 240 extends proximally within hollow shaft 227 to a handle (not shown) wherein a mechanism may be manually operated to move driver 240 within hollow shaft 227, as will be understood by one of ordinary skill in the art of medical stapling devices. In an embodiment, driver 240 and hollow shaft 227 may each be about 30 cm in length. Staple 230 includes two legs respectively having proximally-located expansion bends 236a and 236b connected by a closure bend 237. The two legs of staple 230 respectively have staple expansion ramps 234a and 234b, optional staple tissue stops 238a and 238b, and staple tips 239a and 239b. See step 1010 in FIG. 47.

In practice, the distal portion of stapler 228 is positioned at a preset distance from an arteriotomy, as shown with respect to stapler 128 in FIG. 11. See also step 1020 in FIG. 47. Driver tip edges 242a and 242b abut expansion bends 236a and 236b at the proximal end of staple 230. Staple tips 239a and 239b extend from the distal end of hollow shaft 227, even prior to the initiation of deployment of staple 230 from stapler 228. Driver 240 is advanced distally within hollow shaft 227 such that driver tip edges 242a and 242b push staple 230 distally in the staple chamber formed between actuation tips 229 such that staple expansion ramps 234a and 234b ride along, and are forced apart by anvil 250. The separation of expansion ramps 234a and 234b causes the legs of staple 230 to separate and extend laterally through the open sides, i.e. top and bottom of the chamber along the distal portion of hollow shaft 227. As the legs of staple 230 are spread apart, expansion bends 236a and 236b are forced open and staple tips 239a and 239b separate from each other, as shown in FIG. 16. See also step 1030 in FIG. 47. The deformation of expansion bends 236a and 236b as they are opened may exceed the elastic limits of the staple material such that at least some plastic deformation may occur. Simultaneously, or closely coordinated with the spreading of the staple legs, staple 230 is advanced distally such that staple lips 239a and 239b pierce vessel 102 to engage vessel tissue on either side of arteriotomy 132. See step 1040 in FIG. 47. Stabilization wire guides 114 aid in centering, or stabilizing closure system 122 over arteriotomy 132, as shown in FIGS. 11 and 12. The expanded distance between tips 239a and 239b more than, spans arteriotomy 132, as shown with respect to staple 130 in FIG. 12. As described in the above-mentioned Kanner '356 patent, staple tissue stops 238a and 238b help prevent tips 239a and 239b respectively from fully penetrating the wall of vessel 102 and entering lumen 104.

Figure 13:
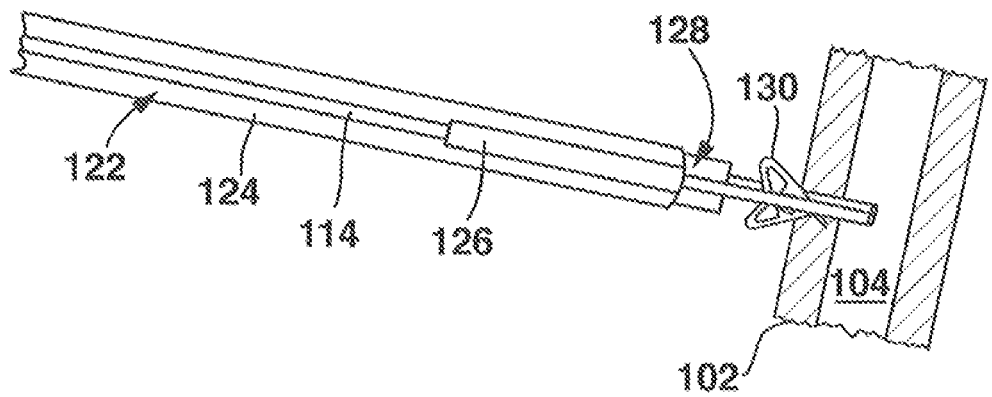
FIG. 13 is a perspective view of the closure system of FIG. 9 with the staple deployed to close the arteriotomy.
Figure 31:
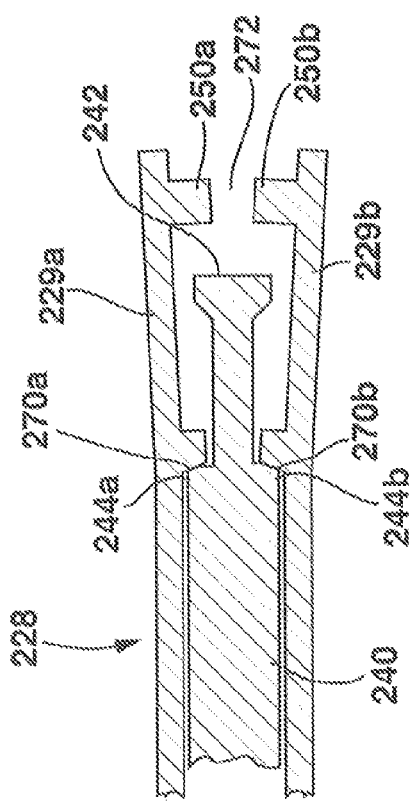
FIG. 31 is a longitudinal cross-sectional view of a top view of an embodiment of a release mechanism for releasing a staple from a stapler of the present disclosure.
Figure 32:
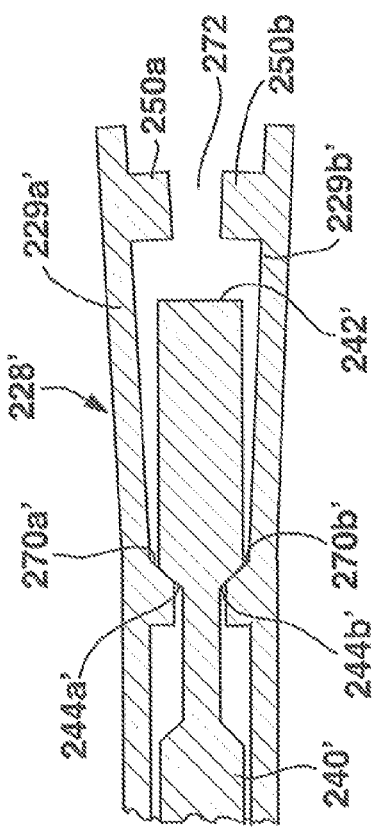
FIG. 32 is a longitudinal cross-sectional view of a top view of the embodiment of FIG. 31 with the actuation tips spread apart.

As driver 240 continues to be moved distally in hollow shaft 227, staple closure bend 237 abuts anvil 250, and staple expansion ramps 234a and 234b clear anvil 250, permitting at least some elastic recovery of staple expansion bends 236a and 236b. See step 1050 in FIG. 47. Driver tip edges 242a and 242b force closure bend 237 against anvil 250, thereby deforming closure bend 237 into a more open angle. The deformation of closure bend 237 may exceed the elastic limits of the staple material such that at least some plastic deformation may occur. Opening closure bend 237 causes the legs of staple 230 to pivot in opposite directions around the apex of closure bend 237 such that staple tips 239a and 239b move toward each other, as shown in FIG. 17. As staple tips 239c and 239b are forced together, the vessel tissue between them is gathered or puckered, thereby closing arteriotomy 132. When staple 230 closes, staple tips 239a and 239b may approach, or touch, or even cross over each other as shown in FIGS. 13, 14 and 17, depending upon the amount of tissue between the tips, First Staple Release Mechanism As staple tips 239a and 239b close toward each other, the proximal portion of staple 230 must be released from stapler 228. Otherwise, as shown in FIG. 17, the proximal portion of staple 230 would be trapped by anvil 250. There are several ways for staple 230 to be released from stapler 228. FIGS. 31 and 32 are top sectional views of stapler 228, with staple 230 being omitted for clarity. Driver 240 may include a distal wedge 244, or distally-facing wedges 244a and 244b, disposed proximally from driver distal edge 242. Wedges 244a and 244b extend laterally outward from side surfaces 246a and 246b of driver 240 in the direction of actuation tips 229a and 229b, respectively. Further, actuation tips 229a and 229b include proximally-facing ramps 270a and 270b, respectively, disposed proximally from anvils 250a and 250b. As described above, driver 240 is moved distally within hollow shaft 227 such that closure bend 237 is opened to force staple tips 239b and 238b together. In a simultaneous movement, wedges 244a and 244b push against and slide along ramps 270a and 270b, respectively, thereby causing actuation tips 229a and 229b to spread apart, from each other, as shown in FIG. 32. With actuation tips 229a and 229b spread apart from each other, a gap 272 is formed between anvil 250a of actuation tip 229a and anvil 250b of actuation tip 229b, thereby releasing staple 230 from the staple chamber of stapler 228. See step 1060 in FIG. 47. Staple 230 is thus permitted to remain in place, closing the arteriotomy as stapler 228, including hollow shaft 227, actuation tips 229a and 229b and driver 240, is removed from the body. With this embodiment, it is important to have close dimensional tolerances between anvil 250 and ramps 270a and 270b, and between driver distal edge 242 and wedges 244a and 244b to ensure coordination between staple deployment and release.

Second Staple Release Mechanism

Figure 33:
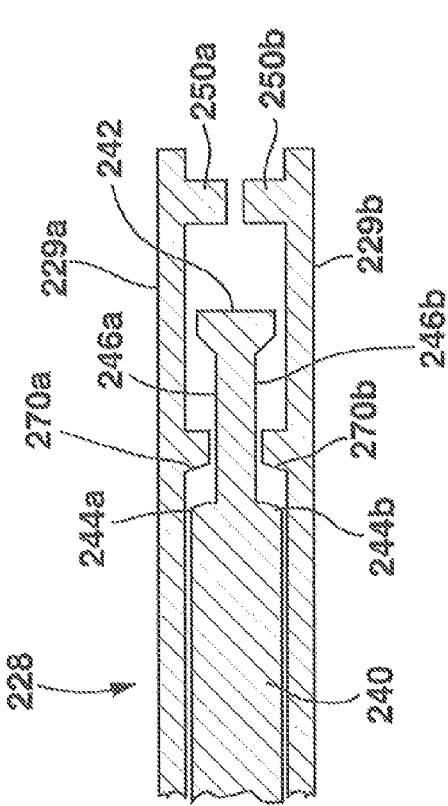
FIG. 33 is a longitudinal cross-sectional view of a top view of another embodiment of a release mechanism for releasing a staple from a stapler of the present disclosure.
Figure 34:
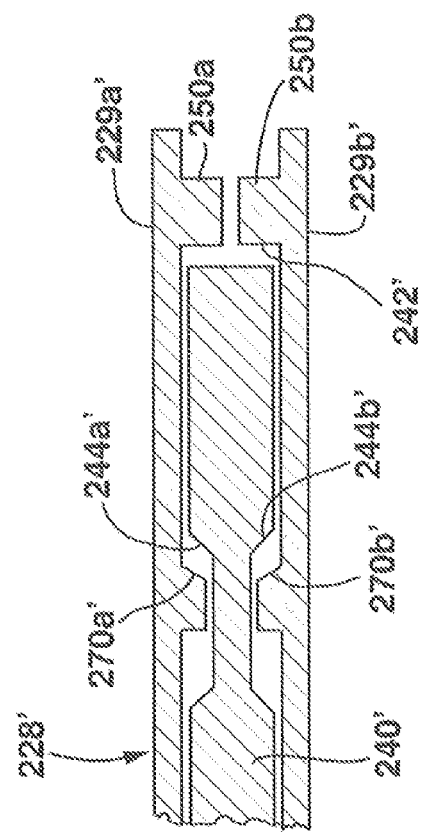
FIG. 34 is a longitudinal cross-sectional view of a top view of the embodiment of FIG. 29 with the actuation tips spread apart.

FIGS. 33 and 34 are top sectional views of another stapler 228', with staple 230 being omitted for clarity. In the embodiment shown in FIGS. 33 and 34, driver 240' includes proximally-facing wedges 244a' and 244b' disposed proximally from driver distal edge 242', and actuation tips 229a' and 229b' include distally-facing ramps 270a' and 270b', respectively, disposed proximally from anvils 250a and 250b. FIG. 33 shows stapler 228' after staple 230 has been deployed, but not released. In order to release the staple from anvils 250a', 250b', driver 240' is moved proximally such that wedges 244a' and 244b' engage ramps 270a' and 270b', respectively. Ramps 270a' and 270b' ride up wedges 244a' and 244b', thereby forcing actuation tips 229a' and 229b' apart from each other and releasing the staple, as shown in FIG. 34. This embodiment is less sensitive to dimensional tolerances than the embodiment shown in FIGS. 31 and 32 because staple 230 is fully deployed before driver 240' is moved proximally to release staple 230.

Third Staple Release Mechanism

Figure 35:
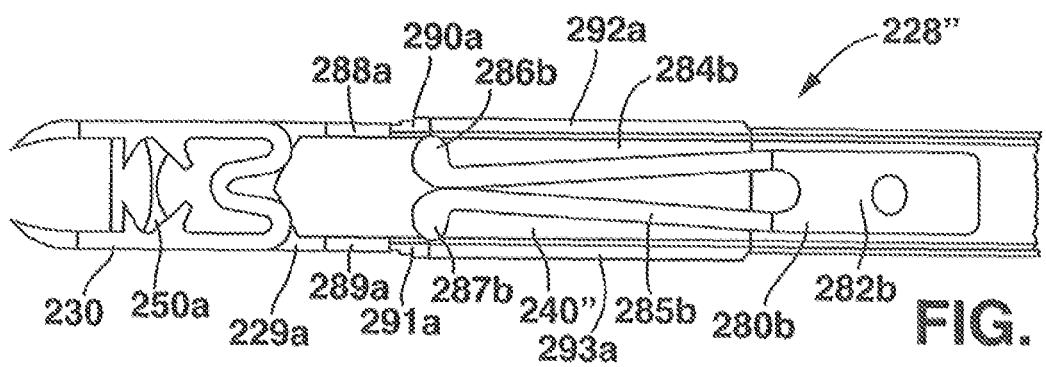
FIG. 35 is a cut-away side view of a stapler with another embodiment of a release mechanism for releasing a staple from a stapler of the present disclosure.
Figure 36:
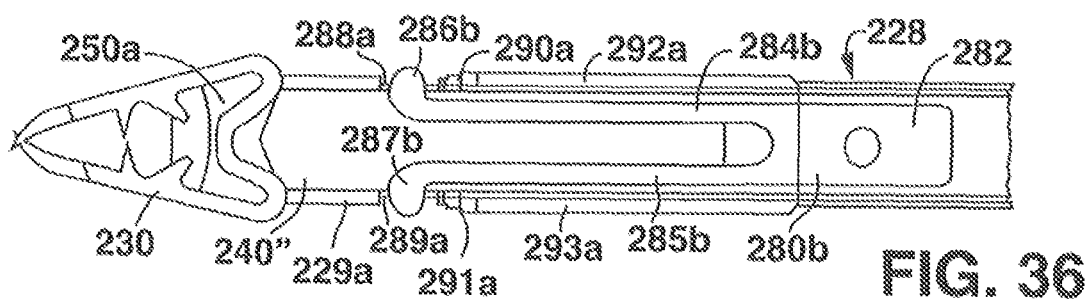
FIG. 36 is a cut-away side view of the embodiment of FIG. 35 with the staple deployed, but not released from the stapler.
Figure 37:
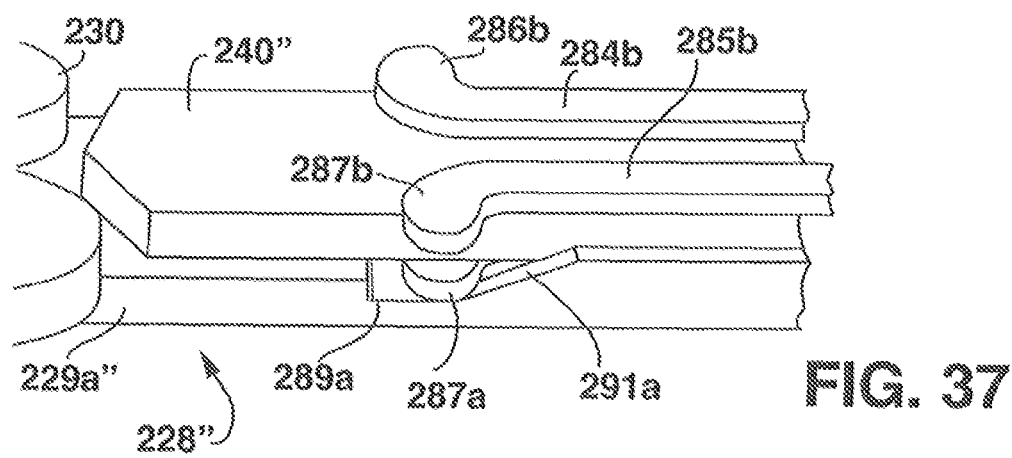
FIG. 37 is a cut-away perspective view of a portion of the embodiment of FIG. 35.
Figure 38:
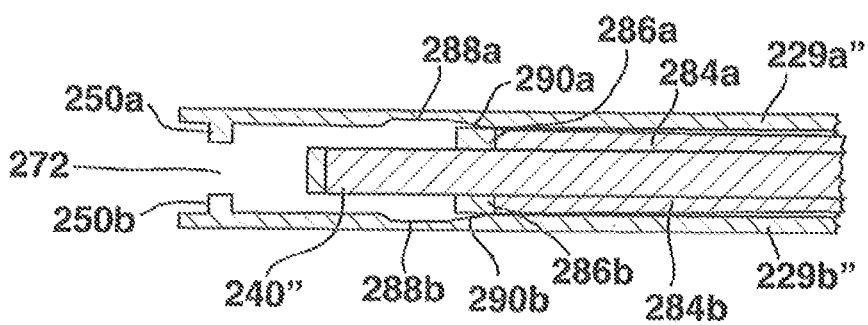
FIG. 38 is longitudinal cross-sectional view of a top view of the embodiment of FIG. 35 with the actuation tips spread apart.
Figure 39:
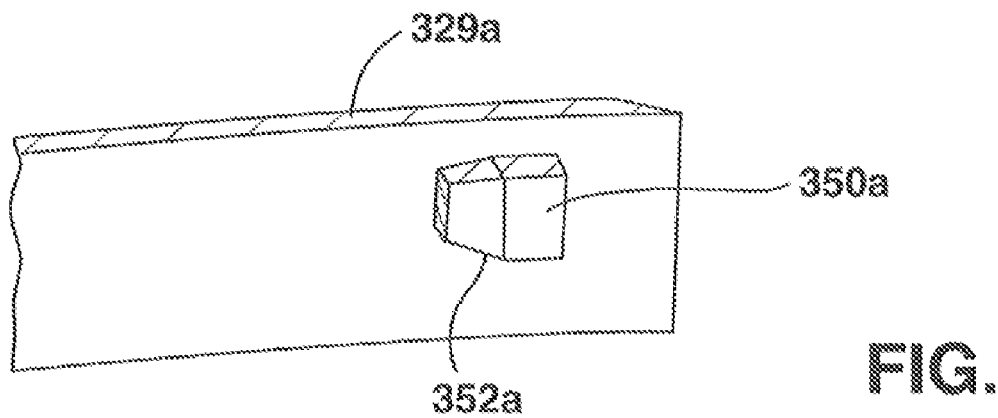
FIG. 39 is a perspective view of an actuation tip of another stapler in accordance with the disclosure.
Figure 40:
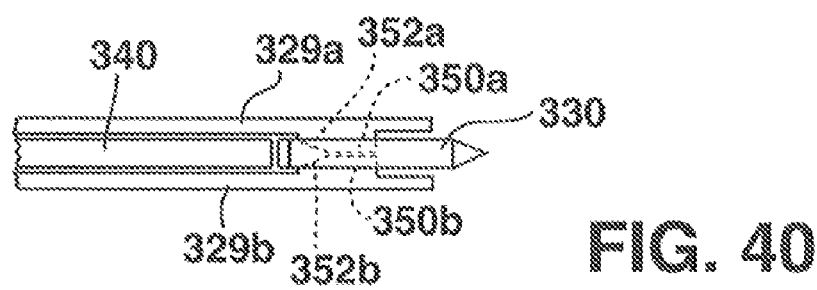
FIG. 40 is a top view of a stapler incorporating the actuation tip of FIG. 39 with the staple deployed, but not released from the staple chamber.

In another embodiment of a stapler 228" shown in FIGS. 35-38, release mechanisms 280a and 280b are provided coupled to each side of driver 240". FIGS. 35 and 36 are side sectional views of stapler 228". Release mechanisms 280a and 280b each includes a base 282a and 282b, a pair of arms 284a/b and 285a/b, and hooks 286a/b and 287a/b extending laterally outward from arms 284a/b, 285a/b, respectively. Actuation tips 229a" and 229b" (only actuation tip 229a" is shown in FIGS. 35-37) include notches 288a/b and 289a/b having ramps 290a/b and 291a/b. FIG. 35 shows stapler 228" with staple 230 in the pre-deployment configuration as stapler 228" is being delivered to the arteriotomy site. Arms 284a/b and 285a/b of release mechanisms 280a/b are resiliently compressed toward each other by sidewalks 292a/b and 293a/b of actuation tips 229a" and 229b". As driver 240" is moved distally within hollow shaft 227" to push staple 230 against anvil 250a/b, hooks 286a/b and 287a/b arrive at notches 288a/b and 289a/b. Sidewalls 292a/b and 293a/b no longer compress arms 284a/b and 285a/b as hooks 286a/b and 287a/b resiliently extend into notches 285a/b and 289a/b, respectively, as shown in FIG. 36. After staple 230 has been deployed to close the arteriotomy, driver 240" is moved proximally, thereby also moving release mechanisms 280a and 280b proximally, as shown in FIG. 37. As release mechanisms 280a and 280b are moved proximally, hooks 286a/b and 287a/b ride up ramps 290a/b and 291a/b. This motion causes actuation tips 229a" and 229b" to spread apart, thereby providing a gap 272 between anvils 250a and 250b through which staple 230 may pass, as shown in the top sectional view of stapler 228" shown in FIG. 38. Note that, as described above, staplers 228, 228' and 228" may include a single anvil 250 extending from one actuation tip toward the other actuation tip instead of a pair of anvils 250a and 250b. Similar to stapler 228' above, stapler 228" is less sensitive to dimensional tolerances because staple 230 is fully deployed before driver 240" is moved proximally to release staple 230.

Staple Materials

Staple 230 may comprise a biocompatible metal such as nitinol (TiNi), stainless steel, tantalum, or titanium. Magnesium or an alloy thereof may also be used to make staple 230, and such materials also have the potential advantage of being bioabsorbable. Staple 230 may also be formed from various filled or unfilled rigid or semi-rigid polymers such as liquid crystal polymer (LCP), polyamide, polycarbonate, polyetheretherketone (PEEK), polysulfone, polyvinylidene fluoride (PVDF), and may include bioabsorbable or biodegradable polymeric materials such as polycaprolactone, poly (glycolide) (PGA), poly(L-lactide) (PLLA) and poly(D,L-lactide) (PLA). In an example of a method of making a staple embodiment of the disclosure, staple 230 may formed of a rigid thermoplastic in an injection mold. Staple 230 may be opened by elastic and/or plastic deformation of expansion bends 236a and 236b and may be closed by elastic and/or plastic deformation of closure bend 237. Combined elastic and plastic deformation refers to a staple that has had its shape changed to exceed the elastic region of its material properties, so the staple will only tend to return part way to its previous shape.

Second Stapler Embodiment

Figure 20:
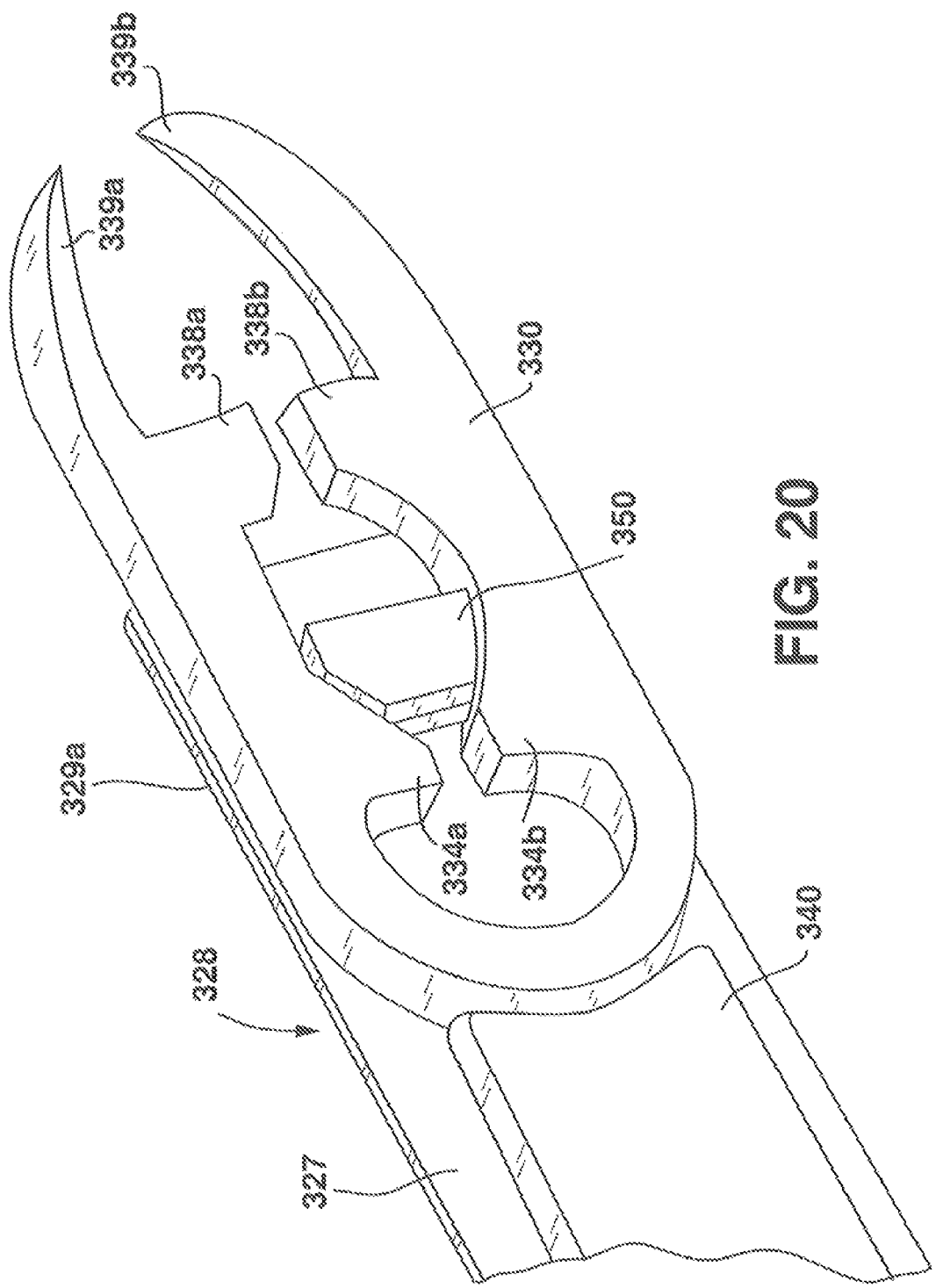
FIG. 20 is a cut-away perspective view of another embodiment of a stapler of the present disclosure.

In another embodiment, FIGS. 20-24 show an embodiment of a stapler 328 of the present disclosure. In particular, FIG. 20 is a cut-away perspective view of stapler 328. Stapler 328 includes an elongate hollow shaft 327 having, at its distal end, a pair of flat opposing actuation tips 329 (only one tip 329a is shown in FIGS. 20-23) spaced apart to provide an open-sided chamber for holding a staple 330. An elongate driver 340 is slidably disposed within hollow shaft 327 and has a flat distal portion slidingly disposed within the chamber. The distal end of driver 340 may be shaped, e.g. concave, for abutment against a proximal bend of staple 330. Anvil 350 for retaining and deflecting staple 330 may extend substantially across the staple chamber and may be integral with or attached to actuation tip 329a, without being affixed to opposite actuation tip 329b. Alternatively, anvil 350 may be formed by two mating anvil halves 350a and 350b, each anvil half being integral with or attached to actuation tip 329a or 329b, respectively, Only one anvil 350a is shown in FIGS. 20-23. Driver 340 extends proximally within the hollow shaft to a handle (not shown) wherein a mechanism may move the driver 340 relative to the hollow shaft and actuation tips 329, as described above with respect to stapler 228.

Stapler 328 includes a staple 330 made according to a material and a process such that it lends to elastically return to a closed shape, as will be described with respect to FIGS. 20-22. Staple 330 may be made of nitinol or other suitable elastic or pseudoelastic shape memory alloy (SMA) that may be heat set in a relaxed or neutral configuration such as the closed configuration shown in FIGS. 20 and 22. Staple 330 is carried within stapler 328 and staple 330 may be heat set in a pre-formed or relaxed configuration with staple tips 339a and 339b crossed over each other, or barely touching each other, or spread slightly apart as shown in FIG. 20. Staple tips 339a and 339b extend from the distal end of hollow shaft 327, even prior to the initiation of deployment of staple 330 from stapler 328. Staple 330 includes two legs connected by a proximal bend. The legs respectively have staple expansion ramps 334a and 334b, optional staple tissue stops 338a and 338b, and staple tips 339a and 339b.

Figure 21:
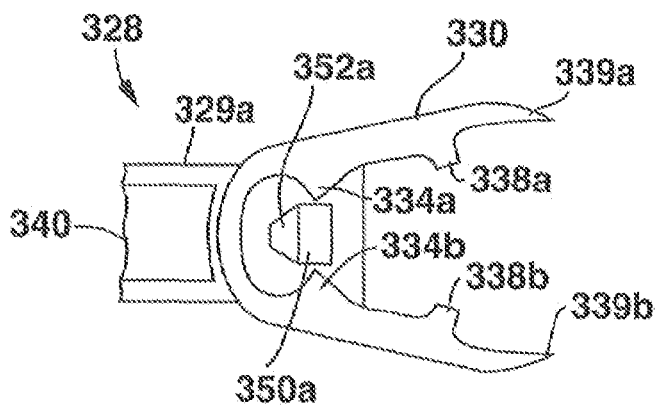
FIG. 21 is a cut-away side view of the stapler of FIG. 20 with the staple being deployed.
Figure 22:
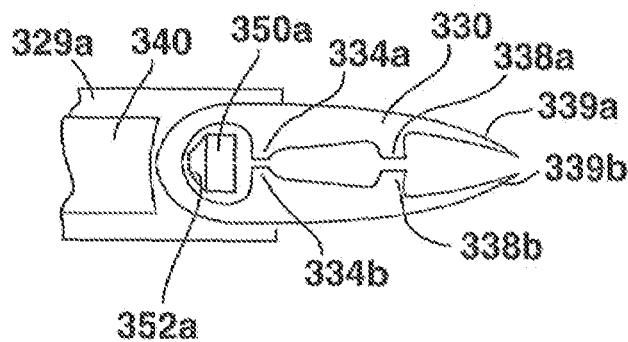
FIG. 22 is a cut-away side view of the stapler of FIG. 20 with the staple closed, but not released.

When stapler 328 is in the proper position with respect to vessel 102, driver 340 is advanced distally within hollow shaft 327 such that the driver distal end pushes staple 330 distally in the staple chamber between expansion tips 329, and staple expansion ramps 334a/334b ride along, and are forced apart by anvil 350, as shown in FIG. 21. The separation of expansion ramps 334a and 334b causes the legs of staple 330 to separate and extend laterally from the open sides of the staple chamber in the distal end of hollow shaft 327. In a simultaneous action, staple tips 339a and 339b are spread apart, the proximal staple bend is opened up, and staple 330 is advanced distally such that staple-tips 339a and 339b pierce the vessel wall (not shown) to engage vessel tissue on either side of arteriotomy 132 (not shown). Referring to FIG. 22, as driver 340 continues to push staple 330 distally, expansion ramps 334a and 334b clear anvil 350, and the elastic or shape memory property of the proximal bend of staple 330 causes staple tips 339a and 339b to close toward each other. As staple tips 339a and 339b draw together, the vessel tissue between them is gathered or puckered, thereby closing the arteriotomy. When staple 330 closes, staple tips 339a and 339b may again approach, or touch, or even cross over each other, depending upon the pre-formed staple configuration and the amount of tissue gathered between the tips.

Figure 23:
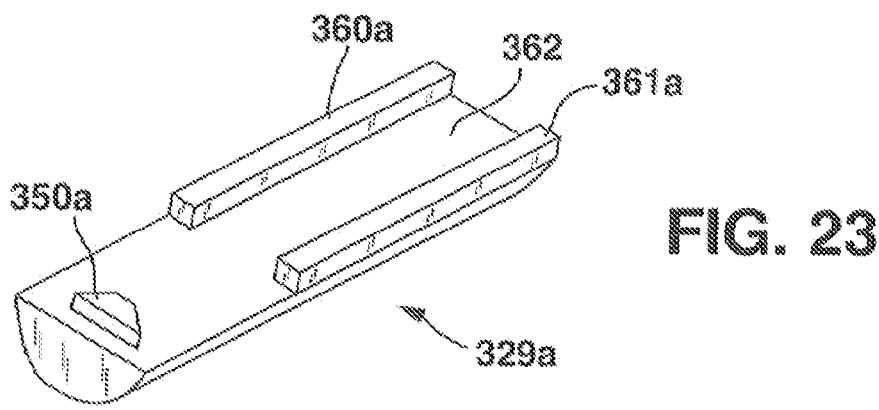
FIG. 23 is a perspective view of an embodiment of an expansion tip of the stapler of FIG. 20.
Figure 24:
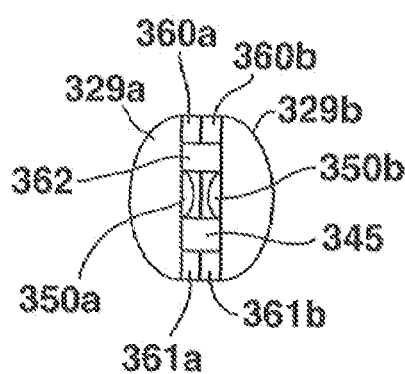
FIG. 24 is an end view of an embodiment of a pair of expansion tips of the stapler of FIG. 20.

The hollow shaft of stapler 328 and expansion tips 329a and 329b may be made of metal or stiff plastic suitable for insertion into the human body, such as stainless steel, nitinol, high density polyethylene, polyamide, or polyethylene block amide copolymer. FIG. 23 shows a perspective view of actuation tip 329a, including anvil 350 and side rails 360a and 361a, which terminate proximally of the distal ends of expansion tips 329a and 329b. Side rails 360a and 361a abut side rails 360b and 361b of expansion tip 329b, as shown in FIG. 24, thus forming passageway 362 there between for slidably receiving the flat distal portion of driver 340. Distally of passageway 362, the flat surfaces of actuation tips 229 form open-sided staple chamber 345, which contains anvil 350. In an alternative embodiment, only one of the expansion tips includes the side rails and the side rails abut against the flat surface of the other expansion tip. In such an embodiment, the side rails may be thicker than in an embodiment with side rails on each expansion tip in order to create the appropriately-sized passageway 362 and staple chamber 345. Although this description of the expansion tips has referred to expansion tips 329a and 329b, it would be understood that it applies equally to expansion tips 229.

Fourth Staple Release Mechanism

Figure 41:
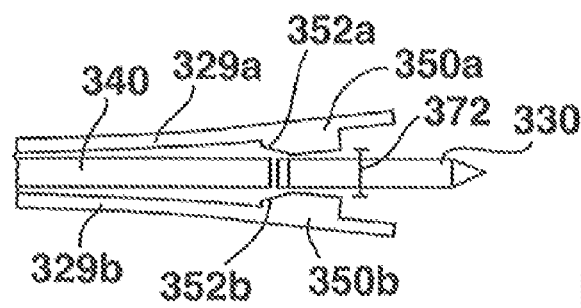
FIG. 41 is a top view of the stapler of FIG. 40, after the staple has been pushed forward to spread apart the actuation tips.

Similar to the description above with respect to staple 230 and FIGS. 15-19, staple 330 must clear anvils 350a/b in order to be released from stapler 328. Such, release can be accomplished by the mechanisms and methods described above with respect to FIGS. 31-45. In particular, anvils 350a and 350b may include proximally-facing ramps 352a and 352b, as shown in FIGS. 20-22 and 39-44. After expansion ramps 334a and 334b clear anvils 350a/b, and the elastic or shape memory property of staple 330 causes staple tips 339a and 339b to close toward each other, as shown in FIG. 22. To release staple 330 from stapler 328, driver 340 may be held in place longitudinally as proximally-directed force is applied to hollow shaft 327. Thus, driver 340 holds staple 330 against, the proximally-facing surfaces of anvils 350a and 350b, and holds staple tips 339a and 339b in the vessel wall about the arteriotomy. In this way, actions taken to release staple 330 from stapler 328 do not pull proximally on staple 330 once it is engaged with the tissue of the vessel wall. However, because the proximally-facing surfaces of anvils 350a and 350b are ramps 352a and 352b, respectively, proximal movement of hollow shaft 327 forces ramps 352a and 352b to separate around the proximal bend of staple 330, thereby causing actuation tips 329a and 329b to spread apart, creating a gap 372 between anvils 350a and 350b, as shown in FIG. 41. As hollow shaft 327 continues to be moved proximally, anvils 350a/b clear staple 330, which is thereby released from stapler 328. Thus, stapler 328 releases deployed staple 330 by forcing actuation tips 329a and 329b to spread apart by engaging ramps 352a and 352b with staple 330 itself. Hollow shaft 327 and driver 340 can then be removed from the body.

Third Stapler Embodiment

Another embodiment of a stapler 428 is shown in FIGS. 42-45. As shown, stapler 428 includes a staple 430 that is similar or identical to staple 330 described above and is made of nitinol or other suitable elastic or pseudoelastic shape memory alloy (SMA). However, staple 430 of the present embodiment can also be similar in shape and material properties to staple 230 shown and described with respect to FIGS. 15-19.

Figure 42:
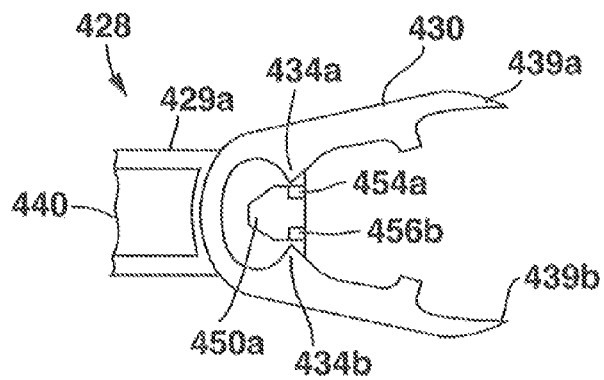
FIG. 42 is a cut-away side view of a stapler with another embodiment of a release mechanism for releasing a staple from a stapler of the present disclosure.
Figure 43:
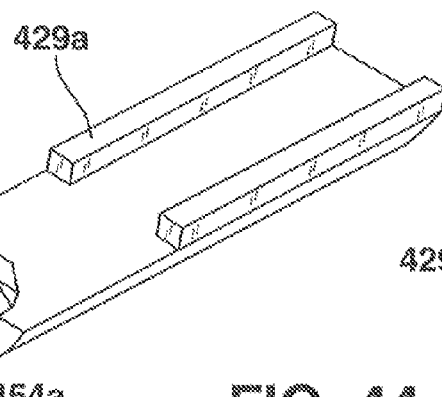
FIG. 43 is a perspective view of an expansion tip of the stapler of FIG. 42.
Figure 44:
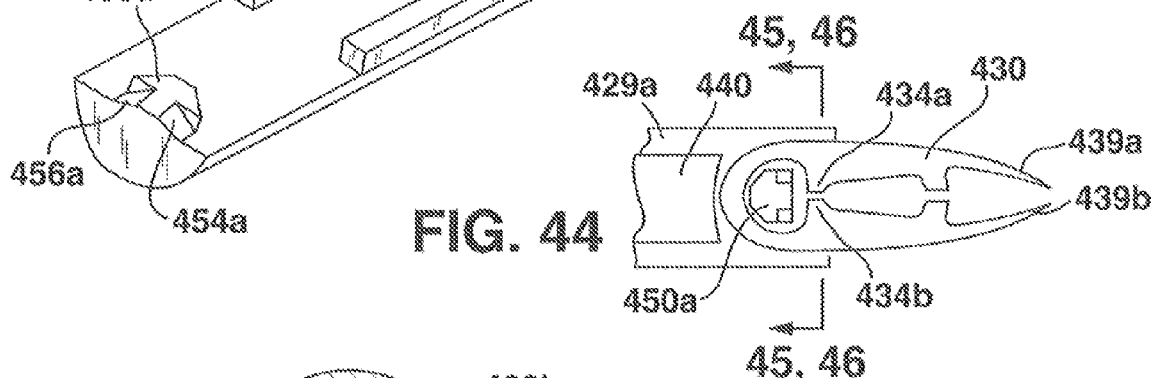
FIG. 44 is a cut-away side view of the stapler of FIG. 42 with the staple closed, but not released from the stapler.
Figure 45:
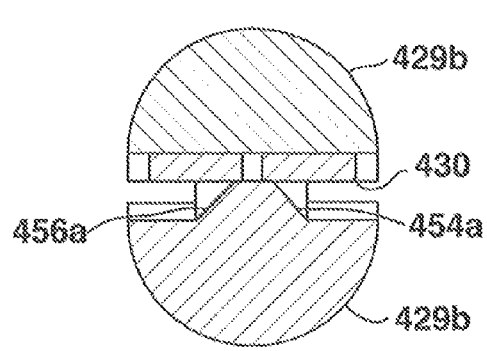
FIG. 45 is a transverse cross-section view along line 45-45 of FIG. 44 with the actuation tip that was cut away from FIGS. 42 and 44.

Stapler 428 further includes actuation tips 429a/b. Only actuation tip 429a is shown in FIGS. 42-44 for ease of viewing, however, it would he understood by one of ordinary skill in the art that actuation tip 429b is a mirror image of actuation tip 429a, as shown in FIG. 43. Actuation tip 429a includes anvil 450a similar to anvil 350a described with respect to FIGS. 20-24. Actuation tip 429a further includes first and second laterally opposed side ramps 454a and 456a disposed abutting the distal end of anvil 450a. Side ramps 454a and 456a may be formed integrally with anvil 450a. Stapler 428 further includes an elongate driver 440 and a staple 430, similar or identical to driver 340 and staple 330 described above with respect to FIGS 20-24. Staple 430 includes staple expansion ramps 434a and 434b.

In use, when stapler 428 is located in the proper position relative to vessel 102, driver 440 is advanced within hollow shaft 424 such that the driver distal end pushes staple 430 distally in the staple chamber between expansion tips 429a/b such that staple expansion ramps 434a and 434b ride along, and are forced apart by anvil 450a/b, as shown in FIG. 42. The separation of expansion ramps 434a and 434b causes the legs of staple 430 to separate and extend laterally from the open sides of the staple chamber in the distal end of hollow shaft 424. In a simultaneous action, staple, tips 439a and 439b are spread apart and staple 430 is advanced distally such that staple tips 439a and 439b pierce the vessel wail to engage vessel tissue on either side of arteriotomy 132. Note that the forces that act to spread apart staple tips 439a and 439b do not act orthogonally to simultaneously spread apart actuation tips 429a and 429b. As driver 440 continues to push staple 430 distally, expansion ramps 434a and 434b clear anvil 450a/b, and staple tips 439a and 439b close toward each other to gather or pucker the engaged tissue, thus closing arteriotomy 132.

Staple 430 may be released from stapler 428 simultaneously with or subsequently to deployment of staple 430 to close arteriotomy 132. Driver 440 may be held in place longitudinally as proximally-directed force is applied to hollow shaft 424 to release staple 430. Thus, driver 440 holds staple 430 in the closed configuration about the arteriotomy. That is, actions taken to release staple 430 from stapler 428 do not pull proximally on staple 430 once it is engaged with the tissue of the vessel wall. As can be seen in FIGS. 42 and 44, when staple tips 439a and 439b close toward each other, the tips of expansion ramps 434a and 434b will also close toward each other and engage first side ramp 454a and second side ramp 456a, respectively. The closing force of staple 430 will wedge expansion ramp 434a between first side ramps 454a/b, and will simultaneously wedge expansion ramp 434b between second side ramps 456a/b. Such wedging action will force actuation tips 429a/b apart.

With actuation tips 429a and 429b spread apart from each other, a gap is formed between anvil 450a of actuation tip 429a and anvil 450b of actuation tip 429b. Hollow-shaft 424 may then continue to be moved proximally over driver 440, such that the gap formed between anvils 450a/b clears staple 430, which is thereby released from stapler 428. Thus, stapler 428 releases deployed staple 430 by forcing actuation tips 429a and 429b to spread apart by the closing force of staple 430 acting against side ramps 454a/b and 456a/b. Hollow shaft 424 and driver 440 can then be removed from the body. The closing force of staple 430 may be an inherent elastic, resilient or shape memory property similar to that of staple 330. Alternatively, the closing force of staple 430 may be the result of moving driver 440 within hollow shaft 424 to plastically deform staple 430 into a closed configuration, as described above with respect to staple 230 shown in FIGS. 15-19. Note that, as described above, stapler 428 may include a single anvil extending from one actuation tip toward the other actuation tip instead of a pair of anvils 450a and 450b.

Center Tube with Staple Protection

In the embodiments described above, closure system 122 may be advanced along stabilization wire guides 114 through tissue track 101 without a sheath placed in tissue track 101. Further, as described above, any one of staplers 128, 228, 328, or 428 may be slidably disposed within center tube 124 and may be advanced through tissue track 101 together with center tube 124. Tips of staples 130, 230, 330, and 430 extend distally from the respective staplers, even prior to initiating deployment of the staples. Thus, while closure system 122 is being advanced to the arteriotomy site, it may be desirable to protect staple 130, 230, 330, or 430 against possible damage from tissue track 101, or conversely, it may be desirable to protect tissue track 101 against possible injury from staple 130, 230, 330, or 430.

Figure 25:
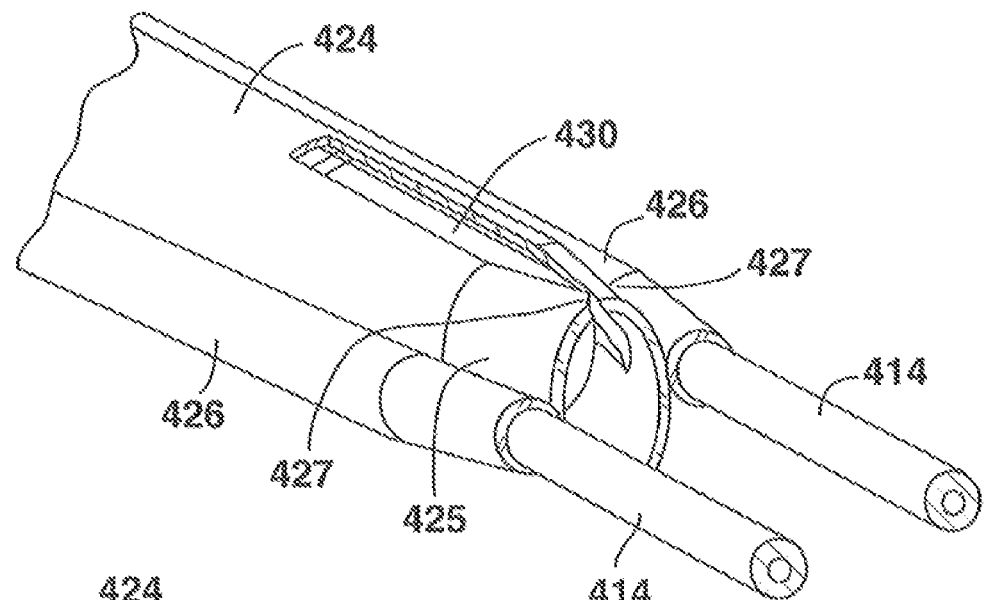
FIG. 25 is a perspective view of a center tube with a pinched distal portion of the present disclosure.
Figure 26:
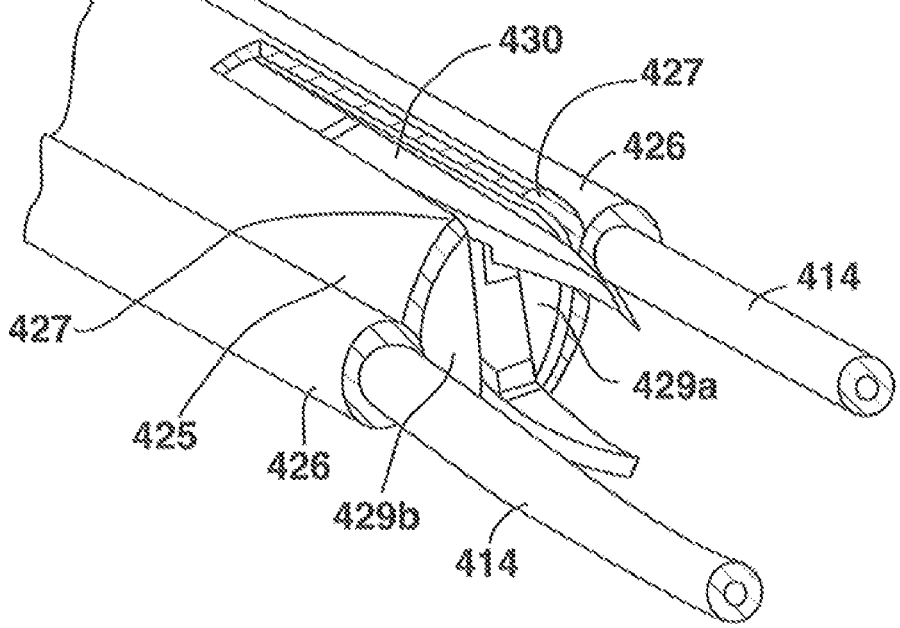
FIG. 26 is a perspective view of the center tube of FIG. 25 during deployment of a stapler.

FIGS. 25 and 26 show an embodiment of a center tube 424 having at its distal end at least two opposing longitudinal slots aligned with the side openings in the staple chamber of staplers 128, 228, 328, or 428, as described above. Center tube 424 further includes a pair of opposing corners 427 defined where each slot meets the distal opening of center tube 424. During staple deployment wherein center tube 424 is advanced close to vessel 102, the legs of staples 130, 230, 330, or 430 can expand laterally from staplers 128, 228, 328, or 428 into the distal slots in center tube 424. In an alternative embodiment shown in FIGS. 11 and 12, the center tube lacks distal slots such that staplers 128, 228, 328, or 428 must be advanced until staples 130, 230, 330, or 430 held in the staple chamber are outside of the center tube before staple deployment is initiated. In this embodiment, the center tube must be spaced away from vessel 102 a sufficient distance such that, during deployment, the stapler can be advanced to the point where a staple can expand laterally without binding on the center tube.

To prevent contact between staple tips and tissue track 101, as discussed above, center tube 424 is provided with an inwardly tapered or pinched distal portion 425, which at least partially covers or guards the staple tips. In the embodiment shown, pinched distal portion 425 brings together corners 427 in center tube 424. As in embodiments described above, center tube 424 is advanced along stabilization wire guides 414 via side lubes 426. Pinched distal portion 425 protects staple 430 from damage while being advanced through tissue track 101, or protects tissue track 101 from injury by staple 430 passing there through. When center tube 424 is advanced to a position outside of the vessel, expansion tips 429a and 429b are advanced distally, opening pinched distal portion 425 and spreading the distal ends of the distal slots in center tube 424, as shown in FIG. 26. Staple 430 is then opened and closed around the arteriotomy as described in the embodiments above.

Alternatively, staple 430 may be deployed without advancing the distal end of the stapler beyond the distal end of center tube 424. In this case, the opposing legs of staple 430 are permitted to expand transversely from the open sides of the staple chamber and to spread through the center tube slots, which are aligned with the open sides of the staple chamber.

Figure 27:
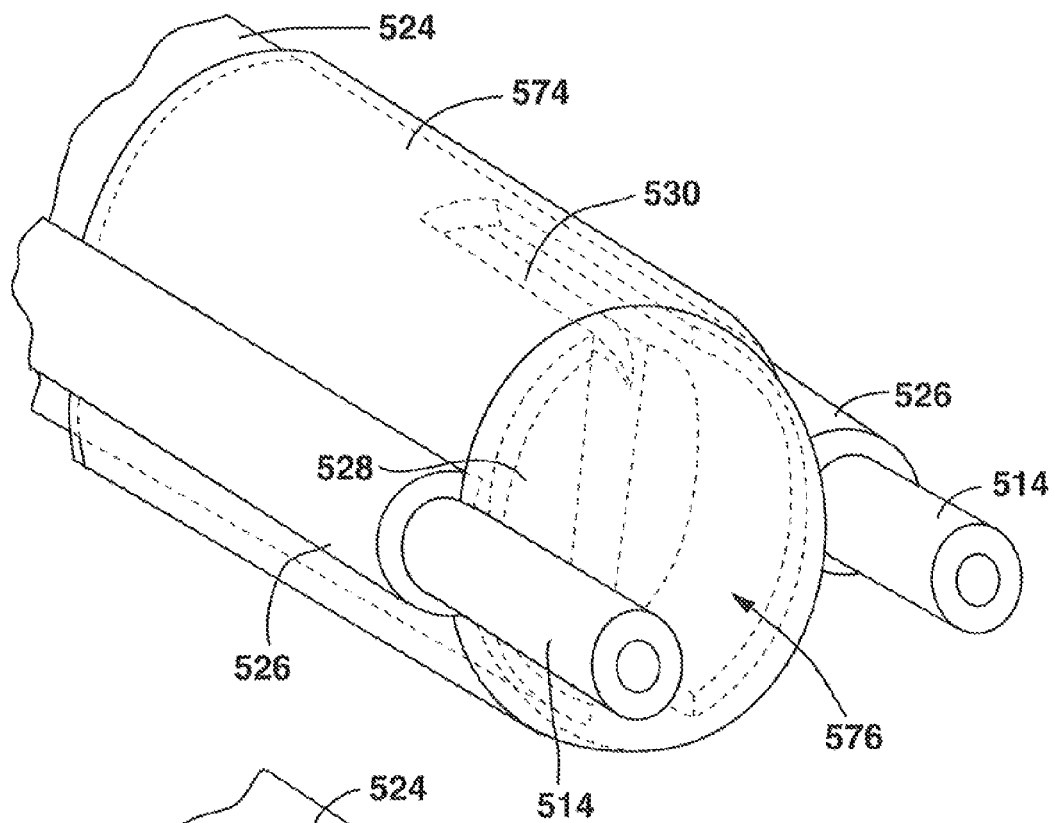
FIG. 27 is a perspective view of a center tube with a frangible cap of the present disclosure.
Figure 28:
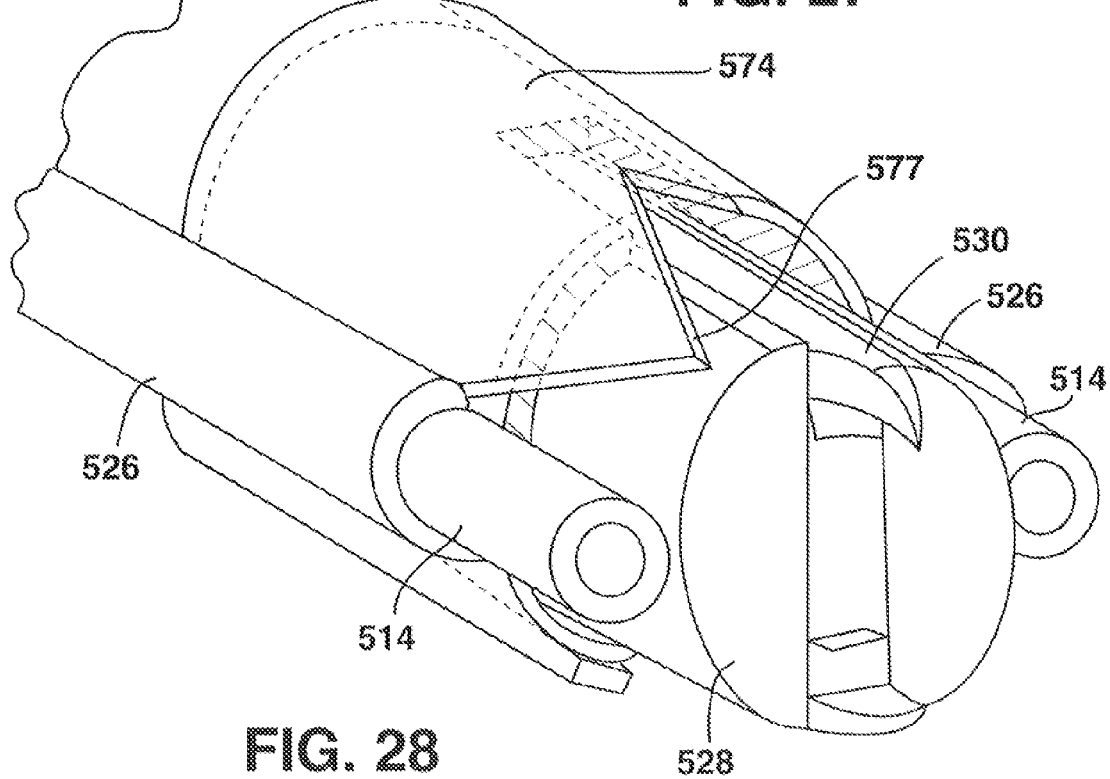
FIG. 28 is a perspective view of the center tube of FIG. 27 during deployment of a stapler.

In another embodiment, the staple may be protected using a frangible cap 574, as shown in FIGS. 27 and 28. Frangible cap 574 is fixed to and covers a distal portion of a center tube 524, and includes a planar portion 576 extending across a distal opening of center tube 524. Frangible cap 574 may be a biocompatible polymeric membrane or a biocompatible metallic foil, and may include perforations, grooves or other disruptions that define tear lines within the cap. Frangible cap 574 may comprise one or more polymers such as polyurethane, polyester or polystyrene. More resilient polymers for making frangible cap 574 may comprise natural or synthetic rubber such as butadiene/acrylonitrile copolymers, copolyesters, ethylene vinylacetate (EVA) polymers, ethylene/acrylic copolymers, ethylene/propylene copolymers, fluorosilicone, latex, polyalkylacrylate polymers, polybutadiene, polybutylene, polyethylene, polyisobutylene, polyisoprene, polyurethane, silicone, styrenebutadiene copolymers, styrene-ethylene/butylene-styrene, thermoset elastomer, thermoplastic elastomer and combinations of the above. Polymeric frangible cap 574 may be formed by various methods including casting, compression molding, liquid injection molding, reaction injection molding (RIM), resin transfer molding (RTM), and thermoplastic injection molding. Polymeric frangible cap 574 may be molded of soft foam, solid elastic material, or a combination thereof.

Frangible cap 574 separates staple 530 from tissue track while center tube 524 is advanced through a tissue track along stabilization wire guides 514 via side tubes 526. Once center tube 524 has been advanced to a position outside of the vessel 102 a stapler 528 carrying staple 530 is advanced distally through center tube 524 such that the staple tips and/or the distal end of stapler 528 penetrate or fracture frangible cap 574, as shown in FIGS. 28 and 44. In the embodiment shown in FIG. 28, as stapler 528 exits the distal end of center tube 524, at least planar portion 576 of frangible cap 574 tears into a configuration having one or more deflectable sections 577 such as flaps that swing, stretch, or otherwise move aside, while frangible cap 574 remains integral and fixed to center tube 524. Staple 530 is then opened, engaged and closed around the arteriotomy as described in the embodiments above.

Figure 29:
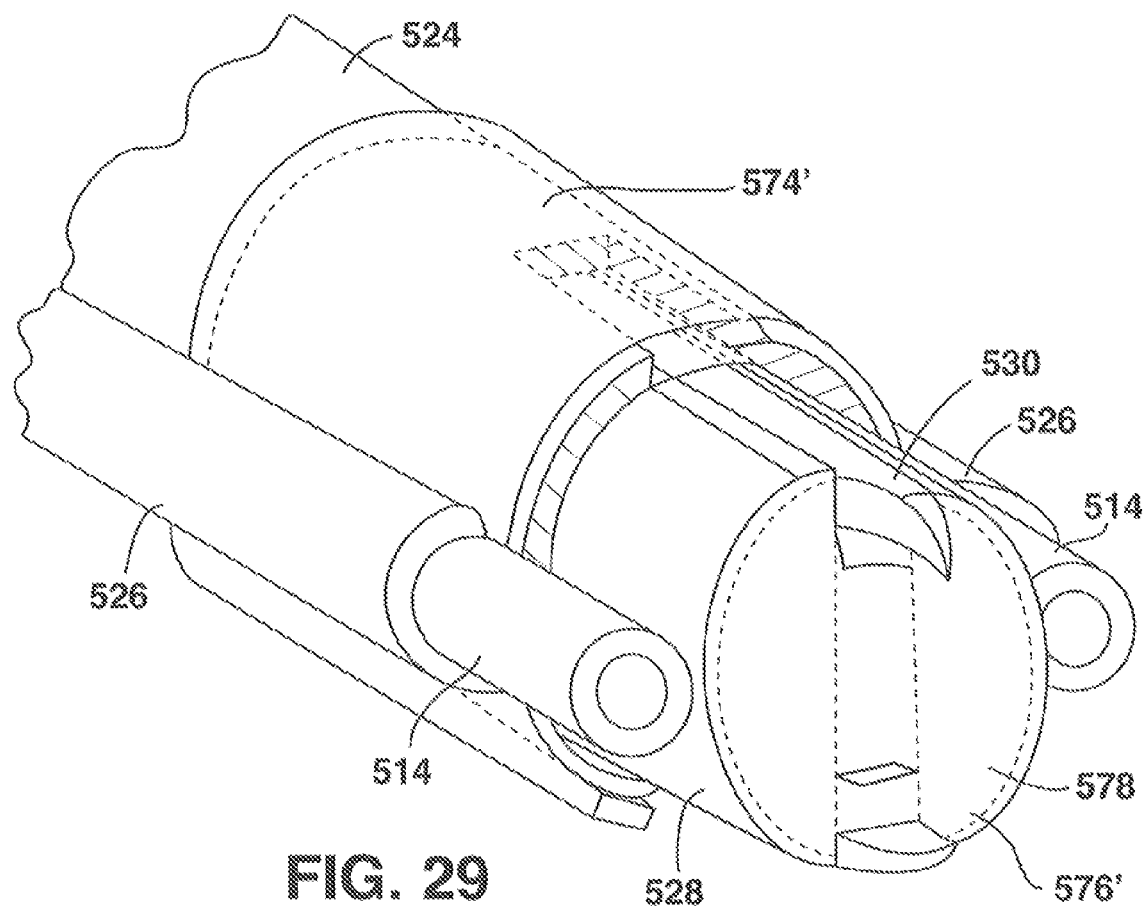
FIG. 29 is a perspective view of another embodiment of the center tube of FIG. 27 with a pledget formed from a frangible cap during deployment of a staple.
Figure 30:
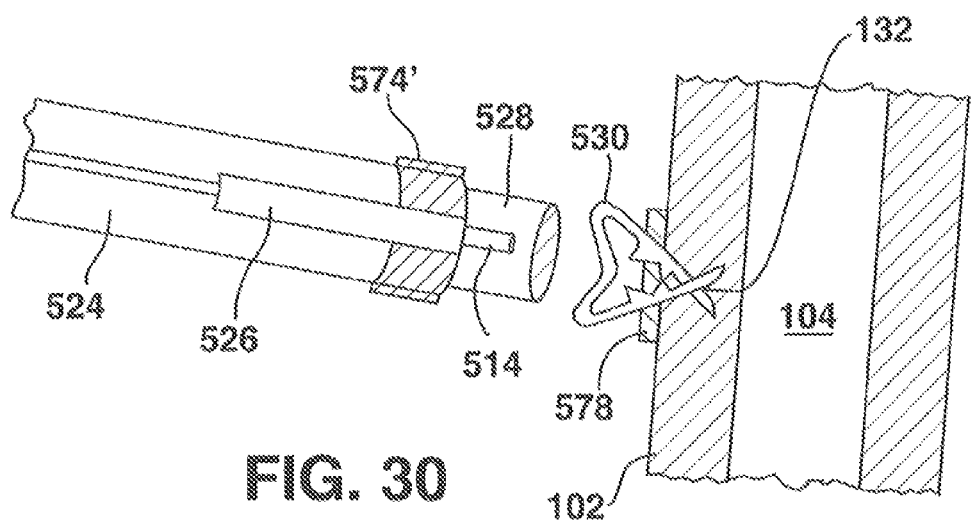
FIG. 30 is a perspective view of the closure system of FIG. 44 with the staple and pledget deployed and the center tube and stabilization wire guides being removed from the body tissue.

In an alternative embodiment of the disclosure shown in FIGS. 29 and 30, as stapler 528 exits the distal end of center tube 524, frangible cap 574' tears into a configuration wherein a generally planar pledget 578 separates from the remainder of frangible cap 574', which stays fixed to center tube 524. Pledget 578 is carried on the distal end of stapler 528 and is implanted with staple 530 to aid in closing arteriotomy 132, as described in U.S. Published Patent Application Number 2004/0093024 A1 to Lousararian et al., the entire disclosure of which is incorporated herein by reference. Pledget 578 may comprise a part of, or substantially all of planar portion 576 of frangible cap 574'. Pledget 578 may have circumferentially spaced notches for frictional engagement with, and centering between the legs of staple 530, as described in the above-referenced Lousararian publication.

As shown in FIG. 30, pledget 578 may promote hemostasis by stemming the flow of blood from arteriotomy 132 that is being closed by staple 530. Additionally, pledget 578 may be either bio-resorbable or non-resorbable, and may include physiologically active agents such as Cefazolin, chlorhexidine, fusidic acid, Novobiocin, polymyxin B, rifampicin, silver or a silver compound, or tetracycline for inhibition of infection. Alternative physiologically active agents may include collagen or derivatives thereof, heparin, or phosphorylcholine for promotion of extraluminal clotting. Such physiologically active agents may be coated onto, absorbed within, or otherwise incorporated into the material of pledget 578.

While various embodiments of the present disclosure have been described above, it should be understood that they have been presented by way of illustration and example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A closure device for an arteriotomy comprising;
   an elongate tube having a distal opening and at least two opposing longitudinal slots extending proximally there from and a pair of opposing corners defined where each slot meets the distal opening of the tube; and
   a staple being slidably disposed within the tube and having at least two opposing legs aligned with the at least two slots, each staple, leg having a tip;

wherein each slot is pinched together adjacent the distal opening such that the opposing corners of each slot converge to cover at least the tip of the respective staple leg.

2. The closure device of claim 1 wherein, the opposing corners of each slot are separable to permit the respective staple leg to pass there between.

3. The closure device of claim 1 wherein the elongate tube includes at least two side tubes for riding along a pair of stabilization wire guides, the side tribes being coupled parallel to, and disposed on opposing sides of a distal portion the elongate tube.

4. The closure device of claim 1 further comprising an elongate stapler slidably disposed within the elongate tube, the stapler comprising;

an elongate hollow shaft and an elongate driver slidably disposed therein;

a pair of opposing actuation tips disposed at a distal end of the shaft and defining an open-sided staple chamber there between, the open sides of the chamber being aligned with the at least two slots in the elongate tube; and an anvil fixedly disposed within the staple chamber;

wherein at least a proximal portion of the staple is held within the staple chamber.

5. The closure device of claim 1 further comprising an elongate stapler slidably disposed within the elongate tube and holding at least a proximal portion of the staple.

6. The closure device of claim 5 wherein the stapler comprises:

an elongate hollow shaft and an elongate driver slidably disposed therein;

a pair of opposing actuation tips disposed at a distal end of the shaft and defining a staple chamber there between; and an anvil disposed within the staple chamber and affixed to one of the actuation tips;

wherein at least a proximal portion of the staple is held within the staple chamber.

* * * * *